US012733835B2

(12) United States Patent
Harmer et al.

(10) Patent No.: US 12,733,835 B2
(45) Date of Patent: Sep. 15, 2026

(54) SYSTEMS AND METHODS OF MANAGING ERRONEOUS SIGNALS IN MARKER-BASED DEVICES

(71) Applicant: Endomagnetics Ltd, Cambridge (GB)

(72) Inventors: Quentin John Harmer, Cambridgeshire (GB); Tiziano Agostinelli, Cambridgeshire (GB)

(73) Assignee: ENDOMAGNETICS LTD (GB)

( * ) Notice: Subject to any disclaimer, the term of this patent is extended or adjusted under 35 U.S.C. 154(b) by 302 days.

(21) Appl. No.: 18/131,126

(22) Filed: Apr. 5, 2023

(65) Prior Publication Data

US 2023/0346251 A1 Nov. 2, 2023

Related U.S. Application Data

(60) Provisional application No. 63/327,637, filed on Apr. 5, 2022.

(51) Int. Cl.

| | |
|---|---|
| ***A61B 5/00*** | (2006.01) |
| ***A61B 5/06*** | (2006.01) |
| ***A61B 90/00*** | (2016.01) |

(52) U.S. Cl.

CPC ............ *A61B 5/062* (2013.01); *A61B 5/7221* (2013.01); *A61B 5/725* (2013.01); *A61B 5/7405* (2013.01); *A61B 5/7435* (2013.01); *A61B 5/7475* (2013.01); *A61B 2090/061* (2016.02); *A61B 2090/3954* (2016.02)

(58) Field of Classification Search

CPC ....... A61B 5/062; A61B 5/7221; A61B 5/725; A61B 5/7405; A61B 5/7435; A61B 5/7475; A61B 2090/061; A61B 2090/3954; A61B 34/20; A61B 5/06; A61B 2017/00725; A61B 2034/2051; A61B 90/98; A61B 2090/397; A61B 34/25; A61B 2017/00119; A61B 2017/00203; A61B 2017/00207; A61B 2090/3908; A61B 2090/392; A61B 2090/3933; G01R 33/1276; G01R 33/16

See application file for complete search history.

(56) References Cited

U.S. PATENT DOCUMENTS 8,174,259 B2 5/2012 Hattersley et al.
8,757,166 B2 6/2014 McKenna et al.
(Continued)

FOREIGN PATENT DOCUMENTS

WO 2022/049395 3/2022

OTHER PUBLICATIONS

Partial Search Report issued by the International Searching Authority for PCT International Patent Application No. PCT/GB2023/050908; date of mailing Jun. 12, 2023; (12 pages).
(Continued)

*Primary Examiner* — Michael J Carey
*Assistant Examiner* — Zainab Mohammed Aldarraji
(74) *Attorney, Agent, or Firm* — K&L GATES LLP

(57) ABSTRACT

In part, the disclosure relates to a method of detecting a marker in a subject in the presence of one or more interfering signals. The method may include detecting a first marker signal; detecting a first interfering signal; comparing one or more characteristics or a metric correlated therewith of the first interfering signal with an interference signal threshold; and generating user feedback based on the comparison and/or movement of a detection probe.

17 Claims, 6 Drawing Sheets

(56) References Cited

U.S. PATENT DOCUMENTS

| | | | |
|---|---|---|---|
| 8,968,171 B2 | 3/2015 | McKenna et al. | |
| 9,234,877 B2 | 1/2016 | Hattersley et al. | |
| 9,239,314 B2 | 1/2016 | Hattersley et al. | |
| 9,687,669 B2 | 6/2017 | McKenna et al. | |
| 9,808,539 B2 | 11/2017 | Shawcross et al. | |
| 10,595,957 B2 | 3/2020 | Mayes et al. | |
| 10,634,741 B2 | 4/2020 | Hattersley | |
| 11,191,612 B2 | 12/2021 | Agostinelli et al. | |
| 11,660,160 B2 | 5/2023 | Agostinelli et al. | |
| 2006/0058604 A1 | 3/2006 | Avinash et al. | |
| 2007/0085528 A1 | 4/2007 | Govari et al. | |
| 2012/0190911 A1 | 7/2012 | McKenna et al. | |
| 2012/0190978 A1 | 7/2012 | McKenna et al. | |
| 2012/0190979 A1 | 7/2012 | McKenna et al. | |
| 2013/0053620 A1 | 2/2013 | Susedik et al. | |
| 2014/0018663 A1 | 1/2014 | Harmer et al. | |
| 2016/0354495 A1 | 12/2016 | Harmer et al. | |
| 2019/0328272 A1 | 10/2019 | Ronen et al. | |
| 2022/0039683 A1 | 2/2022 | Harmer et al. | |
| 2022/0313476 A1 | 10/2022 | Harmer et al. | |
| 2023/0200675 A1 | 6/2023 | Agostinelli et al. | |
| 2023/0277083 A1* | 9/2023 | Harmer .................... | A61B 5/06 600/424 |

OTHER PUBLICATIONS

International Search Report and Written Opinion for PCT International Patent Application No. PCT/GB2023/050908; date of mailing Jul. 20, 2023; (22 pages).

* cited by examiner

G1
Measure signal characteristics using probe
(a set of multiple time and position varying parameters of marker signal)

G2
Determine threshold value or range of values
for a dynamic thresholding variable selected from set G3
Measure the value of the "thresholding variable"

G4
Is the thresholding variable within the desired range?

Yes

No

G5
Filter out interference

G6
Communicate error to user
(such as through GUI / AO changes)

G10
(Optional)
Select new dynamic thresholding variable (targeting a variable specific to marker that is not subject interference as probe position changes)

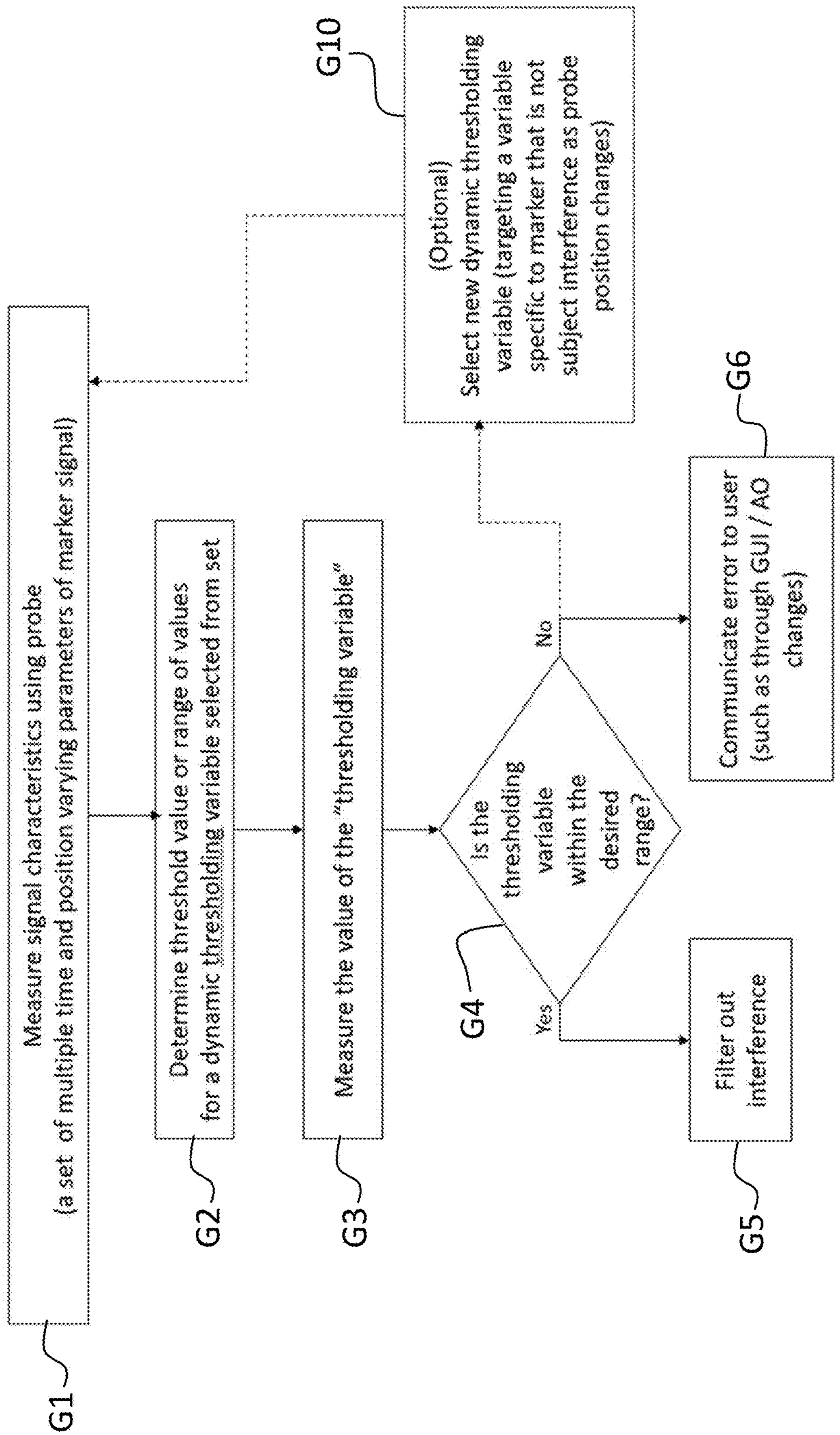

FIG. 10

SYSTEMS AND METHODS OF MANAGING ERRONEOUS SIGNALS IN MARKER-BASED DEVICES

CROSS REFERENCE TO RELATED APPLICATIONS

This application claims priority to and the benefit of U.S. Provisional Application No. 63/327,637 filed on Apr. 5, 2022, the entire contents of which are incorporated by reference herein.

FIELD OF THE DISCLOSURE

In part, the present disclosure relates to the field of surgical guidance, more specifically to systems and methods for detecting markers and tracers that aid in locating a site in the body, for example, a lesion for surgical excision.

Background to the Disclosure Markers may be used to guide surgeons to a region of interest during a surgical procedure, where the site of interest is not physically visible or palpable, for example a small tumour that needs to be excised. Under various circumstances interference, noise, and other extraneous signals can be displayed as an erroneous detection event on some detection system.

Therefore, there is a need for systems and methods that address the challenges associated with erroneous signal detection and interfering signals in general. The present disclosure addresses this need and others.

SUMMARY OF THE DISCLOSURE

In one aspect, the disclosure relates to various hardware, software, FPGA, ASIC, and circuitry based systems and methods that are configured to detect erroneous signals, for example, interference caused by unwanted objects, equipment, or biological material in the vicinity of a probe and/or marker. The disclosure also relates to various system and method embodiments suitable for the filtering of the erroneous signal, the communication to the user that the output signal is erroneous or otherwise reducing or filtering the erroneous signal. In addition, the disclosure describes various user interface features for supporting expedited tracer or marker localization in the presence of interference or other erroneous signals.

In part, in one aspect, the disclosure relates to a method of detecting a marker in a subject in the presence of one or more interfering signals. The method may include detecting a first marker signal; detecting a first interfering signal; comparing one or more characteristics or a metric correlated therewith of the first interfering signal with an interference signal threshold; and generating user feedback based on the comparison and/or movement of a detection probe.

In some implementations of the disclosure, a response signal received from the marker may be determined by a processor to include an interfering signal if and when the value of at least one parameter of the response signal falls outside a range of values that are valid for a given type of marker or a value of a function of two or more parameters of the response signal falls outside a range of values that are valid for a given type of marker according to a predetermined relationship between the parameters. For instance, in some implementations, the two or more parameters may include the amplitude or phase of respective harmonic frequencies of the detection signal, which are known to have a certain mutual relationship for a given marker. This may be especially applicable in the case of detection methods that use susceptometry to localize a magnetic marker that includes a Large Barkhausen Jump ("LBJ") material. If a function of the two or more parameters of the signal at the harmonic frequencies—for example a ratio of the amplitudes of the signal at the different harmonic frequencies—falls outside an envelope of values that are valid for a given marker, then the method includes outputting an alert to the user.

Thus, in one aspect, the present disclosure provides a method of alerting a user when response signal from a probe of a marker localization device is erroneous that includes receiving a response signal from a probe; processing the response signal to measure the values of two or more parameters of the response signal; and outputting a feedback signal signifying an erroneous response signal or ceasing a feedback signal at a user interface when the value of at least one of the parameters falls outside a range of values that are valid for a given type of marker, or a function of the two or more parameters falls outside a range of values that are valid for the given type of marker according to a predetermined relationship between the parameters.

Suitably, the step of outputting the feedback signal may include outputting an audible alert that signifies an invalid response signal and/or displaying on a display text and/or graphics indicating an invalid response signal.

In some implementations, the method of the present disclosure may include outputting a feedback signal signifying an erroneous response signal or ceasing a feedback signal at a user interface when the response signal saturates the signal input. Practically, the method may include outputting a feedback signal signifying an erroneous response signal or ceasing a feedback signal at a user interface only if the response signal saturates the signal input for longer than a predetermined length of time or, where the response signal is repeatedly sampled, if the response signal saturates the signal input for a certain minimum number of successive samples, e.g. for more than 10, 20, 30, 40 or 50 successive samples.

More generally, in accordance with the present disclosure, the relevant value that triggers outputting a feedback signal signifying an erroneous response signal or ceasing a feedback signal at a user interface may include an average value of the relevant parameter or function of two or more parameters over a certain length of time or, where the response signal is converted to a digital signal by an ADC component as described below, over at least a certain number of samples, so the feedback signal signifying an erroneous response signal or cessation of a feedback signal at a user interface is not triggered if the value only transiently exceeds the threshold or falls outside the range of valid values, for example owing to noise or some other temporary extraneous signal.

In another aspect, the present disclosure provides a detection system for localizing a marker in the body, the system includes a response signal input configured to receive a response signal from a probe; one or more processors operable to process the response signal and generate a feedback signal; and a feedback signal output for outputting a feedback signal to a user interface; wherein the one or more processors are configured in use to measure the values of at least two parameters of the response signal and, when the value of at least one of the parameters falls outside a range of values that are valid for a given type of marker, or a function of the parameters falls outside the range of values that are valid for the given type of marker according to a predetermined relationship between the parameters, to output as the feedback signal a signal that signifies an erroneous response signal or to cease outputting the feedback signal.

Suitably, the processor is configured such that when the values of the two or more parameters fall within respective ranges of values that are valid for the given type of marker and the function of the parameters falls within the range of values that are valid for the given type of marker according to the predetermined relationship between the parameters, the processor calculates the proximity of the probe to a marker of the given type based on the value of at least one of the parameters and outputs as the feedback signal a signal representing the proximity.

As mentioned above, in some implementations, the two or more parameters may suitably include respective amplitudes and/or phases of different harmonics of the response signal. The one or more processors may be configured in use to output the signal signifying an erroneous response signal or to cease the feedback signal when a ratio of the amplitudes and/or phases of the harmonics falls outside an envelope of values that are valid for the given marker. This arrangement may be especially, but not exclusively, suitable for use when the marker is a magnetic marker and the detection method uses susceptometry as described herein to determine the distance of the probe to the marker. Preferably the marker may be made of a material with a Large Barkhausen Jump which has been found to produce a response signal with harmonics, even when the magnitude of the driving field is below a threshold required for the domains in the material to flip simultaneously. In methods and systems disclosed herein, the driving field may be driven at an amplitude above or below such threshold. The harmonics may include the first (fundamental) and third harmonics.

In some implementations, the one or more processors may include a filter for removing a first harmonic component of the response signal. Suitably, the one or more processors may include an ADC for converting the response signal to a digital signal; at least one processing unit; and one or more memory devices in electronic communication with the at least one processing unit.

In yet another aspect of the disclosure there is provided a computer program that includes instructions which, when the program is executed by a computer, cause the computer to carry out a method of the present disclosure.

In one embodiment, the user feedback includes removing one or more on screen graphical user interface depictions of a portion of the detection probe or target marker area. In one embodiment, the user feedback is a change to or cessation of auditory feedback being presented to user prior to detection of the first interfering signal. In one embodiment, the method may further include monitoring first interfering signal and repeating comparison until threshold is no longer exceeded. In one embodiment, the method may further include restoring normal probe sensing. In one embodiment, the method may further include setting the interference threshold. In various embodiments, the graphical user interface shown on the display includes distance measurements that change in response to the probe moving closer to and further away from a given marker or tracer.

Thus, in some implementations of the present disclosure, the system may further include as the user interface a display. The one or more processors may be configured to output as the feedback signal a signal containing instructions for the display to display text and/or graphics representing the proximity of the probe to the marker when the values of the two or more parameters and the value of the function of the parameters fall within the respective range of values that are valid, and a signal containing instructions for the display to display text and/or graphics indicating that that the response signal is invalid or to cease outputting the feedback signal when the value of the at least one of parameters or the function of the parameters falls outside the range of values that are valid.

In some implementations, the system may include as the user interface an audible signal generator. The one or more processors may be configured to output as the feedback signal a signal containing instructions for the audible signal generator to emit an audible signal indicating the proximity of the probe to the marker when the values of the two or more parameters and the value of the function of the parameters fall within the respective ranges of values that are valid, and a signal containing instructions for the audible signal generator to emit an audible signal indicating that that the response signal is invalid when the value of the at least one of parameters, or the function of the parameters, falls outside the range of values that are valid.

In one embodiment, setting the interference threshold may include measuring a first set of signal characteristics for a first signal, wherein the first set includes a first marker parameter and a second marker parameter; measuring a second set of signal characteristics for a second signal, wherein the second set includes a first interfering signal parameter; and determining a threshold value or a range of values from the first marker parameter, the second marker parameter, or a combination thereof. In one embodiment, one or more of the measuring steps is performed with a hand-held probe in communication with a non-imaging marker localization/detection system. In one embodiment, one or more of the measuring steps is performed relative to a zone or region within which an interference signal and a marker or tracer signal overlap.

As described above, the first set of signal characteristics for the first signal may include values of first and second marker parameters of the first signal. The two or more marker parameters may have a known relationship for a given type of marker. The relationship may be defined by the physical properties of the marker. For example, it may include a ratio between the values of two characteristics of the signal at two different harmonic frequencies for a detection method using a susceptometry probe to localize a magnetic marker. The first interfering signal parameter may include a function of the two or more parameters. If and when the value of the first interfering signal parameter falls outside (above or below) an envelope of values that are valid for the given marker, the interference threshold is exceeded.

In part, in yet another aspect, the disclosure relates to a detection system for locating markers or tracers in the body. The system may include a filter; a base unit that includes a housing defining a probe interface region and a display interface region; a processing unit disposed in the housing, one or more controls in electronic communication with the processing unit, one or more memory devices in electronic communication with the processing unit; and a probe configured to transmit data to the processing unit and the one or more memory devices, wherein the filter is in electrical communication with the processing unit, wherein at least one of the memory devices includes instructions or electronic circuitry to detect an interference signal that overlaps with a marker or tracer signal in an interference zone; dynamically set a threshold with regard to two or more tracer or marker signal parameters; and if the interference signal has not been filtered or removed, select the marker or tracer signal for localizing the tracer or marker using the threshold. It will be understood that where the value of a ratio of two or more signal parameters is used to determine whether the response signal is valid, the threshold may be dynamic because the range of values that are valid for one of the parameters may depend on the value of one or more others of the parameters.

In some implementations, the processing unit may advantageously be configured to apply a correction factor to the value of at least one parameter of the response signal to attempt to correct the response signal before the system determines the signal is invalid and alerts the user. For example, in some implementations, the processing unit may be configured to adjust the value of at least one of the parameters in accordance with an expected variance between the measured value of the parameter and a valid value. In some implementations, the expected variance may arise as a result of distortion or other unwanted components in a driving signal that drives a driving field in the vicinity of the marker, which causes the marker to produce a responding field. For example, a driving signal for a susceptometry probe may include one or more unwanted harmonic components, but one or more characteristics of such harmonic components may be used to calculate a correction factor by the processing unit which may be applied to correct the response signal by compensating for the unwanted component(s) of the driving signal. Suitable methods and systems for this are disclosed by WO 2021/250485 A1 and U.S. application Ser. No. 17/926,765 (the disclosure of each which is incorporated herein by reference in their entirety).

In some implementations, the processing unit may be configured to process successive portions of the response signal separately and to output the signal indicating an erroneous response signal or to cease the feedback signal only if the response signal is invalid for each portion. The degree of interference to a marker signal caused by an interfering signal from a source of interference may vary according to the strength of a driving field, for example a driving magnetic field, that causes the marker to produce a responding field. Thus, an interfering signal may exceed a threshold for the marker signal to be valid when the driving field is stronger, but not when it is weaker. The driving field may therefore be driven at two or more different amplitudes in succession and if the response signal is determined by the processing unit to be invalid at one of the amplitudes (e.g. a relatively high amplitude), but valid at a different amplitude (e.g. a relatively weak amplitude) then only valid portions of the response signal from the marker during the lower amplitude portions of the driving signal may be used for calculating the proximity of the probe to the marker, while invalid portions of the response signal from the marker during higher amplitude portions of the driving signal may be disregarded. Suitable methods and systems for this are disclosed by WO 2022/049395 A1, and U.S. application Ser. No. 18/024,448 (the disclosure of each of which is incorporated herein by reference in their entirety).

In one embodiment, the probe includes a writable memory device, wherein the writable memory device stores one or more of graphic user interface elements, marker parameters, probe parameters, update scripts, base unit parameters, and probe or base unit specific data files. In one embodiment, the base unit includes a display, the display positioned relative to the a display interface region, wherein the display is configured to display one or more graphic user interface elements that change as the probe moves, wherein the one or more graphic user interface elements. In various embodiments, the display outputs distance measurements indicative of the distance between the probe and a marker that change based on position of the probe. In some embodiments, the display outputs a standby mode display when the probe is a predetermined distance from the marker, wherein the display outputs the standby mode display when an interference signal is detected. In some embodiments, a standby mode display includes a probe representation and a marker representation and one or more distance representations there between.

Although, the disclosure relates to different aspects and embodiments, it is understood that the different aspects and embodiments disclosed herein can be integrated, combined, or used together as a combination system, or in part, as separate components, devices, and systems, as appropriate. Thus, each embodiment disclosed herein can be incorporated in each of the aspects to varying degrees as appropriate for a given implementation. Further, the various apparatus, probes, markers, tracers, filters, housings, displays, processors, software, optical elements, radar-based detection, circuit elements, signal processors, signal generators, auditory feedback, user interface animations and representations, inputs, outputs, variable or dynamic threshold parameters, probe data buffer, components and parts of the foregoing disclosed herein can be used with any probe, detection system, tracker, marker, tracer, or other localization assist technology and other devices and systems without limitation.

These and other features of the applicant's teachings are set forth herein.

BRIEF DESCRIPTION OF THE DRAWINGS

The skilled person in the art will understand that the drawings, described below, are for illustration purposes only. The drawings are not intended to limit the scope of the applicant's teachings in any way.

The structure and function of the disclosure can be best understood from the description herein in conjunction with the accompanying figures. The figures are not necessarily to scale, emphasis instead generally being placed upon illustrative principles. The figures are to be considered illustrative in all aspects and are not intended to limit the invention, the scope of which is defined only by the claims.

FIG. 10 is a process flow chart showing various steps for selecting, evaluating, and updating a thresholding variable to manage and filter interference and/or alert user to presence of interference signal overlapping with marker signal.

DETAILED DESCRIPTION

Figure 1A:
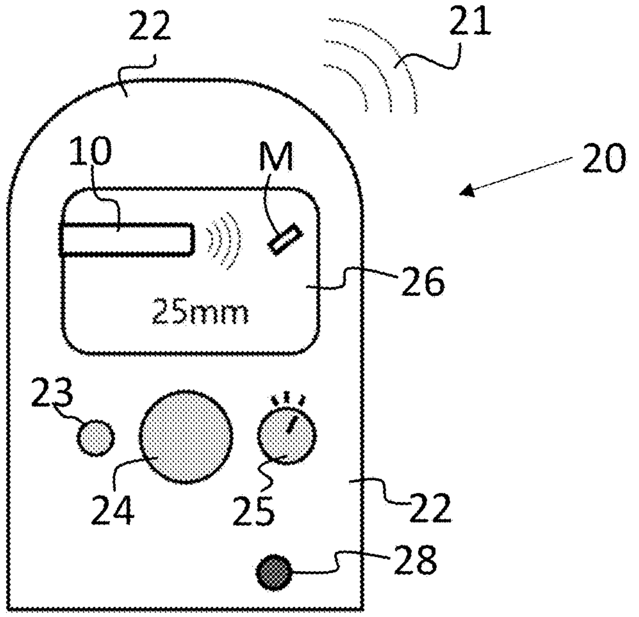
FIG. 1A is a schematic front view of a base unit of detection system for detecting or localizing a marker or tracer according to an exemplary embodiment of the disclosure.

It will be appreciated, for clarity, that the following discussion will explicate various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicant's teachings may not require certain of the specifically described details in every implementation, which are set forth herein only to provide a thorough understanding of the embodiments. Similarly, it will be apparent that the described embodiments may be susceptible to alteration or variation according to common general knowledge without departing from the scope of the disclosure. The following detailed description of embodiments is not to be regarded as limiting the scope of the applicant's teachings in any manner.

In part, the disclosure relates to various systems and methods of detecting a marker or a tracer through one or more signals associated therewith while also simultaneously detecting one or more interfering signals. In various embodiments, the disclosure provides systems, methods, and device to reduce, mitigate, or eliminate one or more such interfering signals or otherwise detect and exclude them.

Markers and tracers are used to guide surgeons to a region of interest during a surgical procedure, where the site of interest is not physically visible or palpable, for example a small tumour that needs to be excised. A marker can also be used to mark a lymph node. In various embodiments, the markers are implantable. Similarly, as another example, a radiopharmaceutical tracer may be injected near a lesion of interest and then, travel to the lymph nodes draining the lesion and accumulating in the vicinity thereof to support detection using a probe-based or other detection system.

In some cases, it is possible for the same detection system to detect both sentinel nodes and lesion markers. For example a, liquid tracer for sentinel node biopsy and a solid marker for lesion localization may be used and both may be detected using the same technology. For example, a liquid radiopharmaceutical tracer and an implantable radioactive seeds can both be detected by a gamma probe. As another example, a magnetic nanoparticle tracer and a magnetic seed can be detected by a magnetic probe. Various types of tracers and seeds/markers may be used that are based on various technologies and related systems and methods of detecting them.

However, various tracer and marker detection methods are often subject to interference signals or other erroneous signals. These unwanted signals can reduce the accuracy or otherwise negatively impact the operation of a feedback system used to guide a user. As the user is performing or about to perform surgery while detecting the presence of tracers or a marker, they must not be distracted from the surgical procedure. Therefore, in part the disclosure relates to user interface features that are suitable for or otherwise configured to be user-friendly guidance during a surgical procedure. A localization feedback system should not require mental processing or overload a user with information in order to distinguish an interference signal from a valid signal. Ideally, the erroneous feedback generated by the interference should be processed, reduced, intercepted, or blocked before being displayed by the user interface of the feedback system.

Preferably, the interference is eliminated or filtered out such that the correct signal is displayed despite the interference. In this way, the interference is hidden from the user. If the interference cannot be eliminated or hidden from the user, the user needs to be informed that there is interference present and that the signal displayed or otherwise communicated to the user may not be correct. In part, the disclosure relates to systems and methods with graphical user interfaces features design to assist an end user with marker or tracer localization when a time sensitive procedure that requires user focus and concentration is underway.

In part, the disclosure provides a non-imaging detection system that integrates an erroneous signal-cancelling module to stop interference from being displayed by the user interface or other features that help address or otherwise manage interference/erroneous signals as part of a marker or tracer detection or localization process. The present disclosure provides various solutions to support users when detecting markers and tracers while also simultaneously being exposed to interfering signals.

Figure 1B:
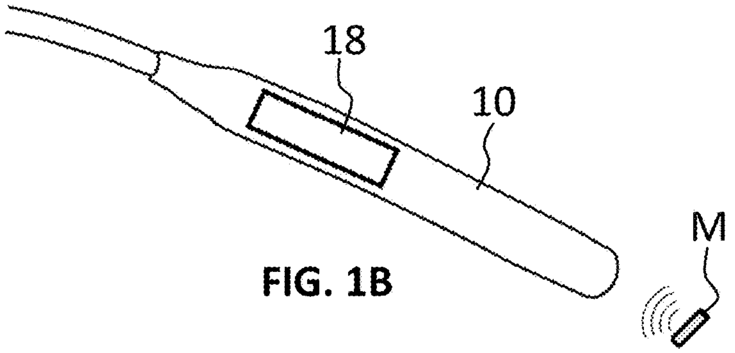
FIG. 1B is a schematic drawing of a detection probe for use with the base unit of FIG. 1A, which is suitable for managing interfering signals to improve detection accuracy according to an exemplary embodiment of the disclosure.
Figure 3:
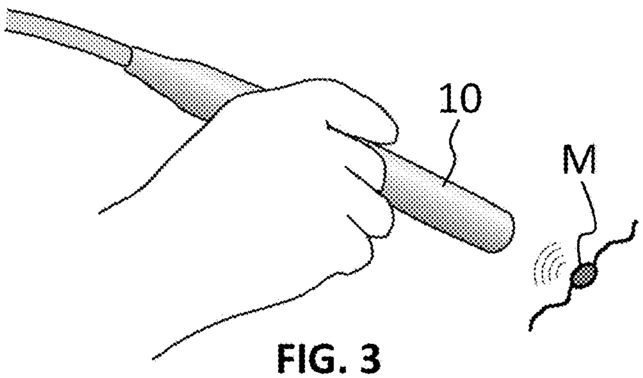
FIG. 3 is a schematic drawing showing how the probe of FIG. 1B can be used in practice to localize a tumour or other lesion in the body according to an exemplary embodiment of the disclosure.

Markers are used to guide surgeons to a region of interest during a surgical procedure, where the site of interest is not physically visible or palpable, for example a small tumour that needs to be excised. Examples of implanted markers (M) are shown in FIGS. 1B and 3. In some embodiments, the terms markers and tracers may be used interchangeably. In some embodiments, tracers refer to detectable material or objects that are injected in a subject and dispersed and/or concentrated in a region where they may be subsequently detected. The marker may be placed during a biopsy or other surgical procedure at a site of interest in the body, for example a cancer lesion. Ideally, such a marker will be deployable through a narrow-gauge needle. The marker is placed under imaging guidance such as ultrasound or X-ray/mammography. During subsequent surgery, the marker is detected and localized using a handheld probe which provides audible, visual, or other feedback to the surgeon to guide the surgery. Typically, the marker is excised along with the surrounding tissue.

A marker can also be used to mark a lymph node before a course of therapy such as, for example, neo-adjuvant therapy. In this way, a node can be readily identified after the therapy for excision, even if fibrosis from the therapy has affected the lymphatics so that conventional lymphatic tracers are not able to flow to the draining lymph nodes. In various embodiments, a probe (10) is used with a base unit (20) as shown in the general embodiment of FIGS. 1A and 1B and a more specific detection system embodiment shown in FIG. 4.

One such tumour-marking approach is to use a marker containing a radioisotope such as Iodine 125 which can be detected using a handheld gamma detection probe, e.g., an electric Geiger or gamma counter. Gamma detection systems may include a handheld probe in communication with a base unit which is used to detect sentinel lymph node tracers in a sentinel lymph node biopsy procedure are known in the art. A radiopharmaceutical tracer is injected near a lesion of interest, travels to the lymph nodes draining the lesion and accumulates there allowing detection. A gamma detection system where the probe communicates via a wireless link may also benefit from the systems and methods disclosed herein.

Magnetic sentinel node tracer detection systems may also benefit from the system and methods disclosed herein. These detection systems may also use a handheld magnetic detection probe in communication with a base unit for sentinel lymph node tracer detection. A magnetic tracer may include superparamagnetic iron-oxide nanoparticles is injected near the lesion, travels to the lymph nodes and accumulates within the nodes allowing the nodes to be identified using magnetic detection.

Also known are systems for lesion localization in which a ‘non-palpable’ lesion (one that is too small to feel or see during surgery) for example, a cancerous tumour or benign lesion, is marked with an implantable marker prior to surgery, and a handheld probe is used during surgery to guide the surgeon to the lesion and allow accurate excision of the lesion while minimizing the amount of healthy tissue that is removed. Several marker detection technologies are known for localizing lesions via detection of an implantable marker:

In some embodiments, the disclosure relates to combination systems that may include imaging technologies such as ultrasound, MRI, or fluorescence imaging suitable to image cancer lesions or lymph nodes while also using one or more detection or feedback systems that enable a marker or tracer to be detected without imaging. A given combination or non-imaging detection system may include features to remove, reduce, block, or otherwise modify the contribution of interference signals or other erroneous signals that may impede or otherwise reduce the accuracy of such marker or tracer detection systems. In many embodiments, the technologies used to detect lesion localization markers or to detect sentinel lymph node tracers are non-imaging detection technologies. In some embodiments, the systems and methods described herein are configured to improve the accuracy of localization or detection of a marker, tracer, or other device using a non-imaging detection modality.

In some cases, it is possible for the same detection system to detect both sentinel nodes and lesion markers. This requires a liquid tracer for sentinel node biopsy and a solid marker for lesion localization, both of which can be detected using the same technology. For example, a liquid radiopharmaceutical tracer and implantable radioactive seeds can both be detected by a gamma probe. Also, a magnetic nanoparticle tracer and a magnetic marker or seed can be detected by a magnetic probe. In various embodiments, the systems and probes disclosed herein are non-imaging detection or localization systems and probes suitable for use with various marker modalities as shown in Table 1 below and otherwise described herein.

However, under numerous circumstances, the tracers and markers detection methods are used in an operating theatre or other clinical environment with various related treatment, patient support, and other technologies, systems and devices that may interfere with accurate detection of tracers, markers, and the associated detection of localization systems and methods.

Some sources of interference are inherent to the system of detection and arise from using a detection method that relies on the same principle or common signal type or detection modality for the marker and the tracer. Therefore, when both the marker and the tracer are placed in the same location, the detection signal may overlap or interfere with the respective detection of each other. In some cases, like in the detection of the marker or tracer magnetic susceptibility, differentiating both signals may be performed by using for example, but not exclusively, the harmonics property, phase or magnetic saturation of the marker or tracer material. For other methods, like in the detection of radioactive seeds and radioisotopes tracers, other unique signals may be used along with modifications to a given detection probe.

As the user is performing surgery while detecting the presence of a tracer or marker, he must not be distracted from the surgical procedure and therefore the feedback system should not require mental processing to distinguish an erroneous feedback signal from a valid feedback signal. Ideally, the erroneous feedback generated by the interference should be eliminated or filtered out such that the correct marker or tracer signal is displayed to the user, or if this is not possible, the presence of interference should be communicated to the user by a user interface in a straightforward way.

FIGS. 5A-D and 6A-D show two different examples of how a graphical and audible user interface may change from depicting a probe converging on a marker by GUI outputs (50, 52*a*; 61, 62), but then encountering interference such as from a metal tray or another implant or some other erroneous signal. In some embodiments, in response to detection of interference or another event of interest, the GUI may be changed to convey that information to the user. In some embodiments, this may be accomplished by removing the probe or another indicia from the user interface as shown in the graphical user interface outputs (53*a*; 63) displayed in FIGS. 5C and 6C. In various embodiments, an audio output (21) from the detection system/base unit (20), such as the system of FIG. 1A is provided that helps a user understand when they are getting closer to a marker or tracer. For example, the rate of a beeping sound may increase or decrease indicating that the probe (10) is moving closer to or away from the marker (M) or tracer, respectively. These sounds may be paired with the graphical user interfaces (GUIs) shown in FIGS. 5A-D and FIG. 6A-D. These GUIs serve as two examples of a user interface being updated in response to the system detecting an interference or erroneous signal. In the GUIs labelled 50; 61 and 52*a*; 62, the probe is being shown as moving closer to a target marker or tracer. For the GUI embodiments of FIGS. 5A-D and 6A-D, to make the presence of interference easier for an end user to understand, the depiction of the probe (10) in the GUI may be removed (53*a*) or the screen (26) may become blank or show a reduced set of information (63).

Figure 5A:
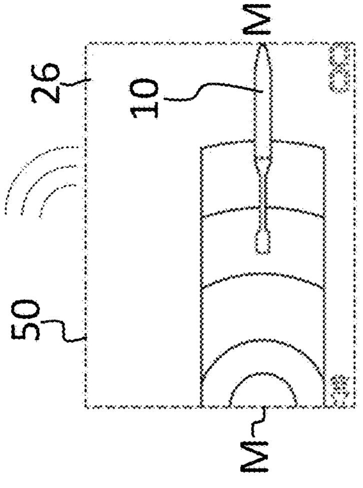
FIGS. 5A-5D show schematically an exemplary sequence of graphical and audible user interfaces suitable for showing the position of a probe relative to a marker or tracer, whereby movement of the probe allows a user to locate the position of such a marker or tracer relative to various types of interference signals and readily understand when interference signals are present according to an exemplary embodiment of the disclosure.
Figure 5B:
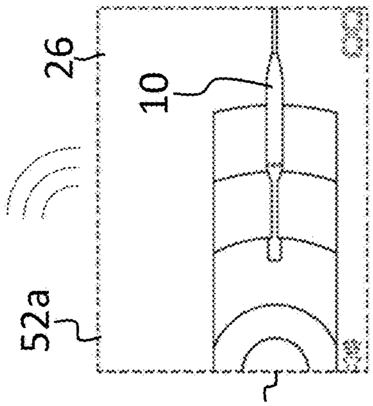
Figure 5C:
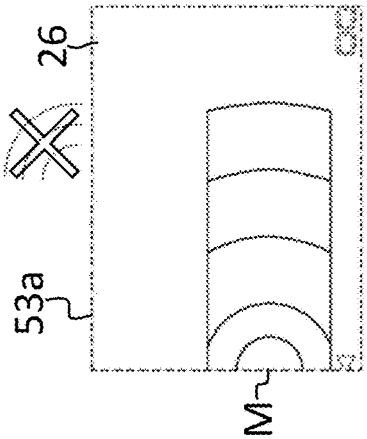
Figure 5D:
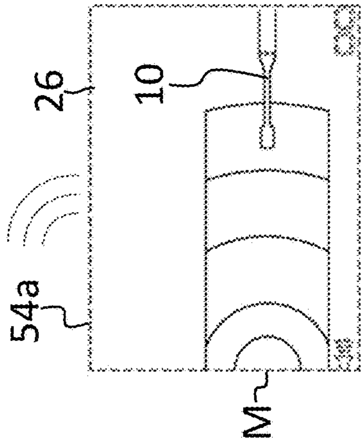
Figure 6A:
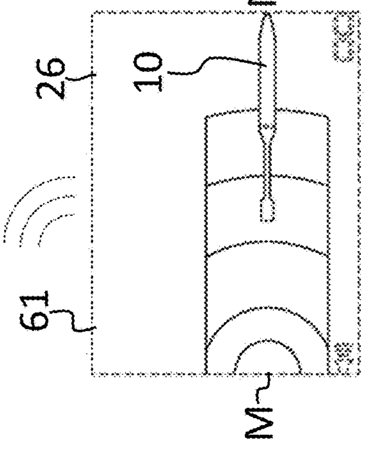
FIGS. 6A-6D show another schematic exemplary sequence of graphical and audible user interfaces of the kind shown in FIGS. 5A-5D according to an exemplary embodiment of the disclosure.
Figure 6B:
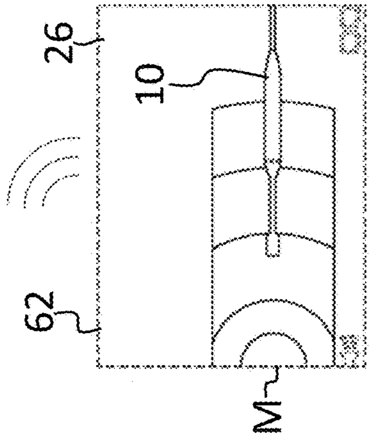
Figure 6C:
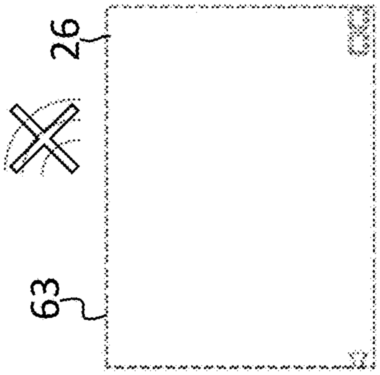
Figure 6D:
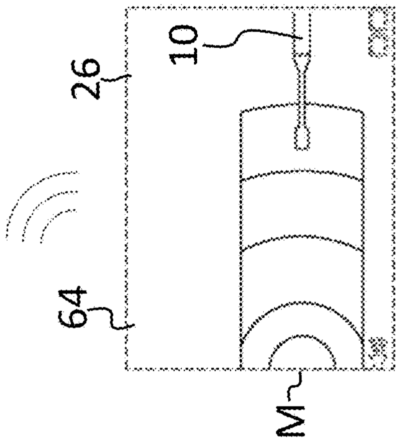

In various embodiments, this change to the GUI may be paired with a change in sound or a cessation of sound, as indicated in FIGS. 5C and 6C. Thus, if a doctor is trying to localize a tumour, and the system detects an interference signal, having the auditory and visual guidance as indicated in screens 53*a*; 63 change or stop, provides a form of easy to understand feedback. Then, in response to moving the probe (10) or the system successfully filtering or otherwise removing the interference, the user interface in screen 54*a*; 64 shows the reinstatement of the graphical cues and the auditory output by which the end user may be guided to the marker or tracer. In some embodiments, a standby GUI that is used when the probe is far from a marker may also be used as the GUI for indicating interference or other events.

The marker and tracer detection usually occurs in an operating theatre where various support structures, surgical instruments, implants, residual solutions or components thereof remain in the tissue after marker delivery or are positioned in the vicinity of the marker or tracer detection device. In various embodiments, the diverse objects in the operating theatre, near the patient, or in the patient can generate interference signals or other erroneous signals that negatively impact the detection system.

In some embodiments, these objects may include metal or magnetic material or particles that interfere with the detection probe and/or detection system. In some embodiments, the interference comes from sources of magnetic field such as permanent magnets used in tool holders or other implants. In some embodiments, the interference may be electromagnetic waves such as gamma, radio, radar or infra-red (IR) waves. Sources of such interference may include gamma rays from radioisotope injections used for sentinel node detection, RF emissions from electronic communications devices, and IR emissions from incandescent light sources or heat sources.

Interference may also come in the form of reflected electromagnetic waves from reflective surfaces near the probe such as surgical instruments. Interference for some sensing technologies e.g., RF and ultrasonic, may also come from a lack of good tissue contact or pockets of air in the transmission path form the probe to the marker or tracer. The sources of interference may interfere with the detection of either markers, tracers, or both, depending on the detection technology and the source of interference.

Other objects and types of markers and their associated detection systems may include magnetic susceptometry, permanent magnet, electromagnetic radiation-based detection, radar-based detection, infrared detection, acoustic or ultrasound detection, RFID-based detection, EM tag based detection, radioactive marker-based detections, combinations of the foregoing, and other maker-based detection modalities.

Certain interference signals may also be small enough to be negligible. Others may be constant within the active area in which detection of a marker or tracer is being performed so that they are not disturbing the basal reference level or create distortion. Various signals that interfere with, degrade, or otherwise reduce the accuracy of a detection system and the sources of such signals may often have some behaviours or other parameters in common. For a given marker, tracer, or other object or device that is positioned in or relative to the patient that identifies a tissue region of interest, each of the foregoing may serve as a source of a signal or other indicator that may be actively or passively detected using one or more systems disclosed herein. Each source may generate, respond to, transmit, or radiate one or more detectable signals. Similarly, certain types of interference signals or other erroneous signals may overlap with, mask, degrade, or otherwise interfere with the detection of a given source signal from a marker or tracer. In some embodiments, the signals associated with a detectable object and signals that interfere with its detection can be shared by several detection methods while other may be more specific to one or several detection methods.

Therefore, there is a need for a non-imaging detection system or a combination system that includes non-imaging features relating to tracer or marker detection that integrates an erroneous signal cancelling module to stop interference or erroneous readings from being displayed by the user interface. The present disclosure aims to address this need and others. Prior to considering interference and erroneous signals in more details, it is informative to consider some detection system embodiments such as those shown in FIGS. 1A and 1B and FIG. 4.

Figure 2:
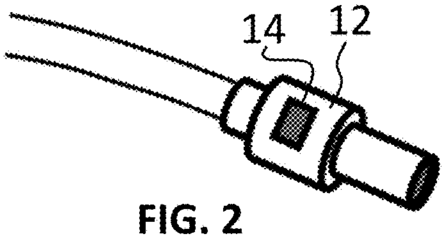
FIG. 2 is a schematic drawing of a probe connector for the detection probe of FIG according to an exemplary embodiment of the disclosure.
Figure 4:
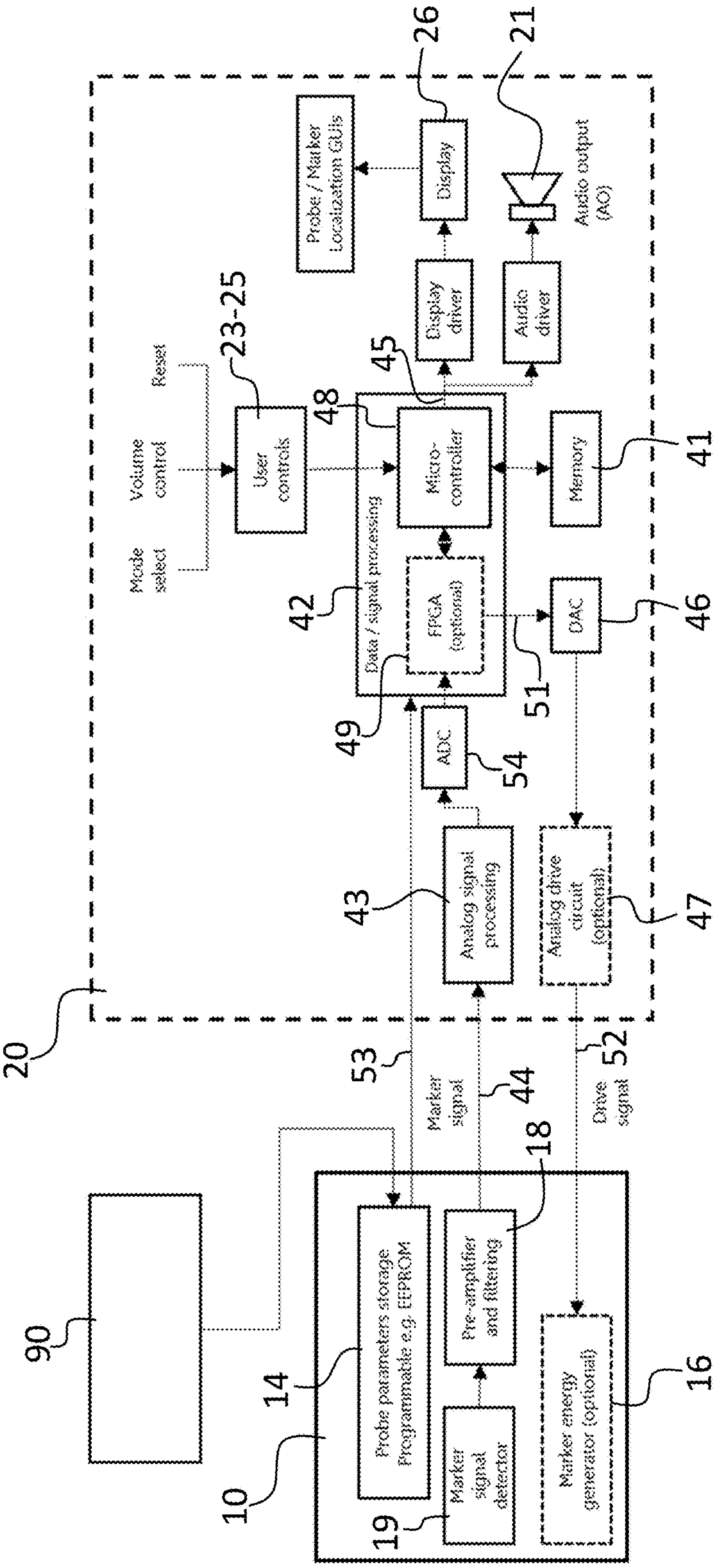
FIG. 4 is a high-level system diagram of a detection system for detecting or localizing a marker or tracer using a probe suitable for also managing interfering signals to improve detection accuracy according to an exemplary embodiment of the disclosure.

Thus, FIGS. 1A and 1B of the accompanying drawings show schematic diagrams of a base unit (20) and probe (10) respectively of a detection system and marker (M) and various components suitable for use with different embodiments. As shown, the probe (10) may be used to detect an implanted marker (M) or a tracer in tissue, such as for example, a tracer in a lymph node. The detection system includes the probe (10) or handpiece and the base unit (20). As shown in FIG. 1A and FIG. 4, the base unit (20) may include a housing (22), a power supply, one or more control systems, electronic memory (41), data storage, one or more processors (42), one or more microprocessors, one or more application specific integrated circuits (ASICs), a signal processor (43), a digital signal processor, one or more user input devices (23-25) such as switch, knob, joystick or touch screen, input signal channel (44), output signal channel (45), and other components as disclosed herein. The base unit (20) may include one or more processors, controllers, microprocessors, boards and busses such that various components are in electrical or optical communication or combinations thereof with each other. The probe (10) may include a probe connector (12) as illustrated in FIG. 2 that may also include one or more devices (14) by which probe parameters, graphic user interface images, scripts, instructions, and patchable and modifiable commands and data structures may be modified using a suitable writing device (90), as indicated in FIG. 4. FIG. 3 shows how the probe of FIG. 1B can be used in practice to localize a tumour or other lesion in the body according to some embodiments.

The detection system thus includes the detection probe (10) connected to the base unit (20) via a wireless or wired connection. The base unit (20) further includes a user interface for providing feedback and information to the user. The user interface may include a visual display/screen (26), the audio interface (21), haptic feedback or other means to communicate with the user. The base unit (10) contains a receiving module to receive a signal from the probe (10), and where necessary amplify it, a microprocessor-driven signal processing module and a module to communicate the signal to the user via a visual display (26) or via audio signals (21) or both. For some technologies such as magnetic detection or radar detection, the base unit (20) further includes circuits or electrical components such as a drive circuit 47 and/or a converter such as a DAC 46 to generate a drive signal to excite the marker via the probe (10). For example, a magnetic susceptometry detection system may include a voltage or current signal generator to generate a waveform to drive a coil (16) in the probe to excite a marker. A radar-based system may contain an RF signal generator to drive an antenna in the probe to create an electromagnetic wave to illuminate a marker.

The detection system may further include a footswitch connected to the base unit (20) via a cable or wirelessly. The footswitch may control one or more functions of the system, for example, to activate the probe, reset the display, change the display mode, activate the erroneous signal cancellation mode, mute the audio signal or another system function.

In some preferred implementations, the system may be used to locate a marker (M) in the body by use of the magnetic susceptometry detection probe (10). The output of the system, for example an indication of the proximity to the marker, position of the marker or distance from the marker to the probe, erroneous signal is displayed on the screen (26) and may also be transmitted in the form of an audible signal (21). In some embodiments, the detection probe may also be used to detect a lymph node that contains a tracer, for example a suspension of iron oxide nanoparticles or radioactive isotopes used for lymph node detection.

The probes and/or detection systems may include one or more switches and visual indicators. The switches (23-25) may be used to control one or more functions of the system, for example, to activate the probe (10), reset the display (26), change the erroneous signal cancellation mode, and/or mute the audio signal (21) or another system function. The visual indicators may be used to indicate the signal from the probe, the proximity or direction of the marker from the probe or indicate battery life or another aspect of the function. The indicators preferably include LEDs.

Often, the handheld probe includes an EPROM or other read and writable memory device (14) that has some or all characteristics or parameters for the thresholds and for defining the marker detection algorithm for use with that handheld detection probe. The threshold may be different for different probes using the same method and the EPROM can identify the probe and its specific characteristics. This allows for the calibration of the system.

Referring to FIG. 4, of the accompanying drawings, a block diagram of a detection system according to an embodiment is illustrated. In some embodiments, the system of FIG. 4 may depict a magnetic and tracer detection probe or a marker detection or system detection system using a different technology. As shown in FIG. 4, the probe (10) may be a wired or wireless probe that measures, detects, or otherwise generates data in response to signals that change with the proximity of the probe to a given marker or tracer. A given probe suitable for detecting any of the markers or tracers disclosed herein may include a pre-amplifier (18), a filter, and combinations thereof. The pre-amplifier (18) may be used to amplify a drive signal (44) leaving the probe or a signal being detected as part of a localization process to locate and zero in on the location of a implanted marker or a tracer that is present in particular region or volume of tissue. Similarly, as shown in FIG. 2, the probe (10) may include a probe connector (12) with a wireless transmitter or otherwise suitable for connecting to the detector based unit (20) at a probe connector socket. In some embodiments, the probe may have a probe connector (12) that includes an electronic device and/or a circuit-based device (14) that includes readable and writeable memory such as an EEPROM. The data stored in the probe's EEPROM (14) may be used to update the base unit (20) and may be configured so that all new probe sizes and models may work with the base unit and changes the thresholds, marker signal characteristics, or process steps disclosed herein. In some embodiments, a new probe design will include new graphical user interface face elements such the probe may be shown and animated with distance information on the display screen. These user interface elements may be stored on the EEPROM (14) of the probe.

A given detection/localization system may include a base unit (20) and at least a marker detection probe (10). The marker detection technology, probe, and marker may use gamma detection also known as radioisotope detection; magnetic field detection; Eddy current detection; RF, radar or other electromagnetic detection; RFID tag detection; resonant magnetic tag detection, or another suitable non-imaging detection technology.

As illustrated in FIG. 4, the base unit (20) includes the caseworks or housing (22) of the base unit (20), a main processing unit (42), a display (26), a loudspeaker (21) or other audio output, user controls (23-25), analogue signal processing (43), and marker detection technology-specific analogue signal processing. The housing may define various regions, displays, and opening for ports and connectors.

Further as shown in FIGS. 1A and 4, the user controls will typically include a mode select switch (25) to select which probe and detection technology to use, a volume control (24) to alter the volume of the audio output (21) and a reset button (23) to allow a detection mode to be reset or set to zero where required. The volume control (24) may also include a feature to mute or unmute the audio output. The user controls may further include a footswitch (not shown) with switches or other foot-operated controls to fulfil one or more of the user control functions.

The main processing unit may include one or more electrical/electronic circuits and a microcontroller (48) such as the STM32F769 microcontroller from STMicroelectronics. The microcontroller controls and interacts with a computer memory (41) for example formed of SD RAM and is part of a digital signal processing unit that may additionally or alternatively include a Field Programmable Gate Array (FPGA) (49). The microcontroller (48) or FPGA (49) generate an initial drive signal appropriate for the mode that has been selected via the mode select switch.

The base unit (20), user controls (23-25) and main processing unit (42) are common for both the tracer detection and the marker detection, thus reducing the amount of circuitry and software in the system and reducing the complexity and cost of the overall system.

This non-imaging magnetic tracer detection system is not to be confused with magnetic resonance imaging systems (MRI). MRI systems provide images based on the excitation of water molecules in tissue and can be used to image cancers, for example breast cancers. Iron oxide particles are known in the art to provide enhanced contrast in MRI images following intravenous injection of the particles. In the present disclosure, however, the tracer is injected locally near a lesion, not intravenously, and the tracer is detected by non-imaging magnetic detection.

Magnetic Detection Mode

When detecting a magnetic marker or tracer, the initial drive signal (51) is converted to an analogue signal (52) via a digital to analogue converter (DAC) (46) and then the drive circuit amplifies (47) the signal and, where necessary, filters the signal to optimise its purity. The amplified drive signal (52) drives the energy generator (16), to create the desired alternating field. However, in some embodiments the signal may be generated away from the probe (10), for example in a pad or mat underneath the patient (not shown). In either case, where the marker includes a Large Barkhausen Jump material, the driving field may suitably be driven above or below the threshold at which the domains of the magnetic material flip polarity. Not every detection technology utilises a drive signal and so it is to be appreciated that this part of the system is only employed in some embodiments.

Also in the handheld detection probe (10), there is provided a magnetic signal detector (19), typically a coil or coils configured to detect magnetic fields in the vicinity of the probe (10), and preferably also may include an amplifier (18) to increase the magnitude of a detected response signal (53) before it is transmitted to the base unit (20). In the base unit, the response signal (53) may be further amplified and filtered in the analogue signal processing unit (43) before being digitised by an analogue to digital converter (ADC) (54). Still referring to FIG. 4, further signal processing may also happen in the digital signal processing unit (42), and this may involve any of filtering, demodulation, a lock-in amplifier, and other means of isolating the signal from sources of noise and converting it into an output signal. Suitably, the further processing may include measuring the amplitude and/or phase of the response signal (53). For example, where the marker is formed of a Large Barkhausen Jump material, the further processing may include measuring the amplitude and/or phase of two or more harmonics of the response signal, typically the first and third harmonics.

In some embodiments, the microcontroller (48) communicates the output signal (45) to the display (26) and audio output (loudspeaker) (21) to give the user an indication of the proximity of the probe (10) to the marker (M) or tracer, position of the marker or tracer or distance from the marker or tracer to the probe. A user may selectively move the probe (10) in an effort to determine if movements of the probe result in a graphic user interface and/or an auditory output indicative of the user's movement of the probe is getting closer to or further away from the marker/tracer, as shown in the user interfaces and auditory outputs shown in FIGS. 5A-D and FIGS. 6A-D.

The various optional and typical components of the various marker/tracer detection or localization system of FIGS. 1A, 1B, 2, 3 and 4 and the use of graphic user interface changes in response to an interference signal as shown in FIGS. 5A-D and FIGS. 6A-D may be applied to various marker detection systems.

Table 1 below includes various examples of different detection systems and marker modalities and various associated sources of interference/erroneous signals and detection methods relating thereto. These may be used to trigger interference/erroneous signal detection based on positional information relating to various zones as described below in more detail with regard to FIG. 4.

Table 2 below includes an exemplary summary for some embodiments that identifies high (H) and low (L) marker distances relative to an interference source zone. The exemplary data in Table 2 may be used to evaluate the distances of a marker (M) that is detectable based on magnetic susceptibility or other detection modalities disclosed herein to define the position of the detection probe (10) relative to the marker and an interference source (I) in various zones, such as the zones depicted in FIG. 7.

Interference signals or other erroneous signals that may be defined differently, depending on the detection method used to locate markers or tracers, but in some cases may share common parameters or be described using similar positional information, zones, and other reference frames.

Several detection methods are known in the field of surgical marking and can be grouped based on their fundamental principles. A first group uses the magnetic susceptibility; a second group generates a responsive identifying signal when interrogated with a signal from a detection system; a third group uses a permanent magnet; a fourth group uses reflective properties such as radar waves or infrared; a fifth group detects the generation of specific radio or electromagnetic waves; and a sixth group is focused on the detection of gamma waves. Other detection methods and groups are also described herein, and the systems and methods disclosed herein may be applied generally to various detection systems and interfering objects.

TABLE 1

Interferences for main solutions in the field of medical markers and tracers

| Processor/ Detection System and related marker/ tracer detection modality | Magnetic AC Susceptometry | Permanent magnet | Radar/IR | RFID | EM tag | Radioactive |
|---|---|---|---|---|---|---|
| Source of interference/ erroneous signal | Metal (tools, retractors, implants, tables, tissue perfused with magnetic material, etc.) | Magnetic fields (medical device, tool holder) | (1) Incandescent light (2) Radar reflective surface (change in tissue properties) | EM absorbing objects EM interference NFC | Same as RFID | Gamma source (shine through from injection site) |
| Interference/ erroneous signal detection method | Harmonic amplitude and/or phase Threshold detection | Field magnitude Array of sensors to distinguish local from general fields | (1) Amplitude of radar and/or IR response (2) Phase of radar | Presence or absence of signal Pulse sequence response | Same as RFID + drop in resonant response | Spectra of emissions (e.g. $TC_{99}$, $I_{131}$) |

TABLE 2

| | | Interference Source Zones | | |
|---|---|---|---|---|
| | | High | Low | Out of range |
| Marker (seed/tracer) Zones | High (H) (e.g., <about 3 mm) | Zone 1 Interference detected and filtered out | Zone 2 Interference detected and filtered out | No interference detected |
| | Low (L) (far but detectable) | Zone 3 Unacceptable interference detected → cut out | Zone 4 Interference detected but small enough to be acceptable | No interference detected |
| | Out of range (e.g., >about 40 mm) | Zone 5 If tool is very close then may create spurious signal | Zone 6 Interference detected and filtered out | No interference detected |

Interference zones—Zones define the position of the detection probe relative to the marker and interference source These different groups of detection methods will be impacted by different kinds of interference signals, phenomena, and other erroneous signals or noise effects. One or more types of interference may radiate from a sole source or a cluster of sources and have one or more similar overlapping patterns with the signal generating marker or tracer.

Figure 7:
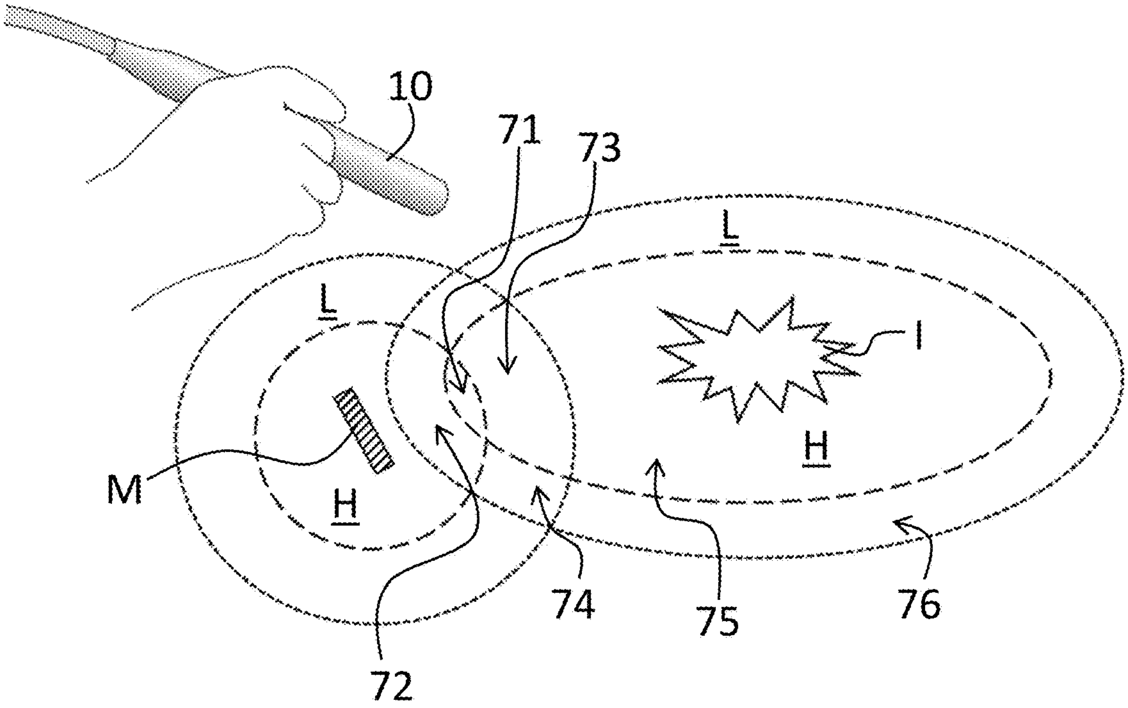
FIG. 7 is a schematic diagram of a hand-held probe suitable for use in localizing a marker that works with signals from the probe and/or other sources to detect the marker relative to a source of interference or other erroneous signal according to an exemplary embodiment of the disclosure.

As shown in FIG. 7, various sources of interference (I) will generate a zone of high interfering signal intensity, a zone of lower interfering signal intensity and a zone of negligible interfering signal intensity. Similarly, the marker (M) or tracer will generate a zone of higher detection signal intensity, a zone of lower detection signal intensity and a zone of negligible signal intensity.

Generally, the closer the source of interference (I) is to the probe (10), the higher the interference or 'noise;' and the closer the probe is to the marker (M) or tracer, the stronger the signal from the marker or tracer. The ability of the detection system to display the correct signal is typically dynamically related to the signal-to-noise ratio ("SNR"), i.e., the ratio of the signal strength to the level of interference or other erroneous signals that degrade detection performance. If the marker or tracer is close to the detection probe, the probability to detect the correct signal increases. By contrast, if the source of interference is far away, the likelihood of being able to eliminate or filter out the interference increases.

Conversely, if the marker (M) or tracer is further away from the detection probe (10), the signal is harder to detect, and if the source of interference (I) is close to the detection probe, it will be harder to filter out the interfering signal. Thus, the relative positions of the marker or tracer and the source of interference with respect to the detection probe affect the ability of a given detection system to display the correct signal, an erroneous signal, or an alert that there is interference present. The relative positions of the marker or tracers and a given source of interference or an erroneous signal may be described relative to various different spatial zones. In various embodiments, zones may overlap and include transitional regions from one zone to another.

Zones that overlap with or extend from the source of interference and zones generated by the marker or tracer will overlap, to define two or more different zones with various levels of overlap between the detection signal and the interference signal. For ease of reference, some exemplary zones are described herein and depicted in FIG. 7. A given zone is typically associated with a position relative to the handheld detection probe, the marker or tracer being detected and the source of interference.

An interference or erroneous signal or reading zone may extend from a source of interference such as a retractor, a metal table, or an implant. A marker or tracer zone may extend from the one or more of the markers or tracers, or the various markers disclosed herein. In some embodiments, determining zones of interference or signal overlap with a marker or tracer signal of interest is used to inform user actions relative to a user interface. A given reference to a zone such as "first zone", "Zone A", or "Zone 1", relative to other zones is arbitrary and different zones may be used according to increasing or decreasing or other numbering or labelling schemes for distinguishing the zones without limitation.

Still referring to FIG. 7, in various embodiments, a zone such as Zone 1 (71) represents a region of strongest signals overlap, with the high interfering signal intensity joining the high detection signal intensity. In various embodiments, a zone such as Zone 2 (72) is an overlap between the low interfering signal intensity and the high detection signal intensity. In various embodiments; a zone such as Zone 3 (73) is an overlap between the high interfering signal intensity and the low detection signal intensity. In various embodiments, a zone such as Zone 4 (74) is an overlap between the low interfering signal intensity and the low detection signal intensity. In various embodiments, a zone such as Zone 5 (75) includes or only includes the high interfering signal intensity without any overlap. In various embodiments, a zone such as Zone 6 (76) includes or only includes the low interfering signal intensity without any overlap between a high interference signal and a high marker or tracer signal. In some embodiments, evaluating and/or resolving overlapping, interfering, or competing marker signals and/or erroneous signals in Zones 1, 2, 4 and 6 (71, 72, 74, 76) may be addressed using the systems, methods and other features described in WO 2021/250485 A1, U.S. application Ser. No. 17/926,765, WO 2022/049395 A1, and U.S. application Ser. No. 18/024,448 (the disclosure of which is incorporated herein by reference in their entirety).

In some embodiments, the zones that include the low (L) or high (H) detection signal intensities without any overlap between such high and low signal intensity have not been identified nor discussed in detail because, with respect to such zones, the lack of overlapping marker signals of interest and interfering signals need not be processed or analyzed to identify the marker signal and will not be discussed in depth as they do not require any processing of the interfering signal. In some embodiments, when high and low signal intensities, magnitude or other signal specific characteristics or sets thereof are discussed, the use of the terms high and low are to contrast various values or parameters relatively to the other. For example, a given system or method embodiment is configured to address various scenarios when a marker or tracer signal is difficult to resolve because of another interfering or erroneous signal. Thus, if a metallic retractor or another source of interference is higher relative to the marker signal, then the marker signal is lower relative thereto and at risk for being harder to detect in light of the presence of a higher interference signal. This problematic scenario occurs in Zone 3 (73), for example, in FIG. 7.

As shown, in Zone 3 (73), there is a high interference signal extending from source of interference and this region of high interference overlaps, in part, with a low region of marker of tracer signal intensity. As a result, in Zone 3, in the absence of the application of one or more of the method or system embodiments disclosed herein, it may not be possible to filter out the interfering signal from the detection signal. By contrast, if a marker signal is higher than a lower interference signal, there may not be a need for further processing or analysis by the detection/localization system in order to be able to zero-in on the marker or tracer of interest.

In Zone 1 (71), the detection signal is strong enough to allow the differentiation and filtering out of the interfering signal. In Zones 2 (72) and 4 (74), the interfering signal is at a lower level, also allowing its differentiation and filtering out from the detection signal. To filter out the interfering signal, various methods and algorithms may be used, such as for example, those described in WO 2021/250485 A1, U.S. application Ser. No. 17/926,765, WO 2022/049395 A1, and U.S. application Ser. No. 18/024,448 (the disclosure of each of which is incorporated herein by reference in their entirety).

Zone 5 (75) still produces a spurious signal that cannot be filtered out, but this usually occurs outside the surgical site when the probe is close to the source of interference (I), thus causing erroneous feedback that is easy to understand by the user. Conversely, the interference occurring in Zone 3 (73), which cannot be rectified, is commonly occurring within the surgical site and therefore the user must be alerted about the erroneous signal feedback.

The processing of the interfering signal may use one or more signal characteristics that follow a certain pattern to identify the interference so that it can be filtered out or so that the marker signal may be selected directly. Preferably, the processing of the marker signal may use two or more signal characteristics that have a predetermined relationship to each other to identify interference. If and when one or more of the signal characteristics fall outside a range of values that are known to be valid for a particular combination of probe and marker, for example if the signal consistently saturates the system input, the signal is assessed to be invalid. Further, if a function of the two or more characteristics, for example a ratio of two or more parameters of the response signal, falls outside an envelope of values that are known to be valid for the marker and probe, then the signal is assessed to be invalid. Such a ratio is especially useful, because an extraneous interfering field will affect the characteristics differently according to the strength of the response; the use of two or more characteristics that behave in a known way relative to one another allows them to be cross-checked to assess their validity. If the ratio or other function of the two or more parameters falls outside an envelope of values that are known to be invalid, the presence of an interfering signal can be inferred.

Figure 9:
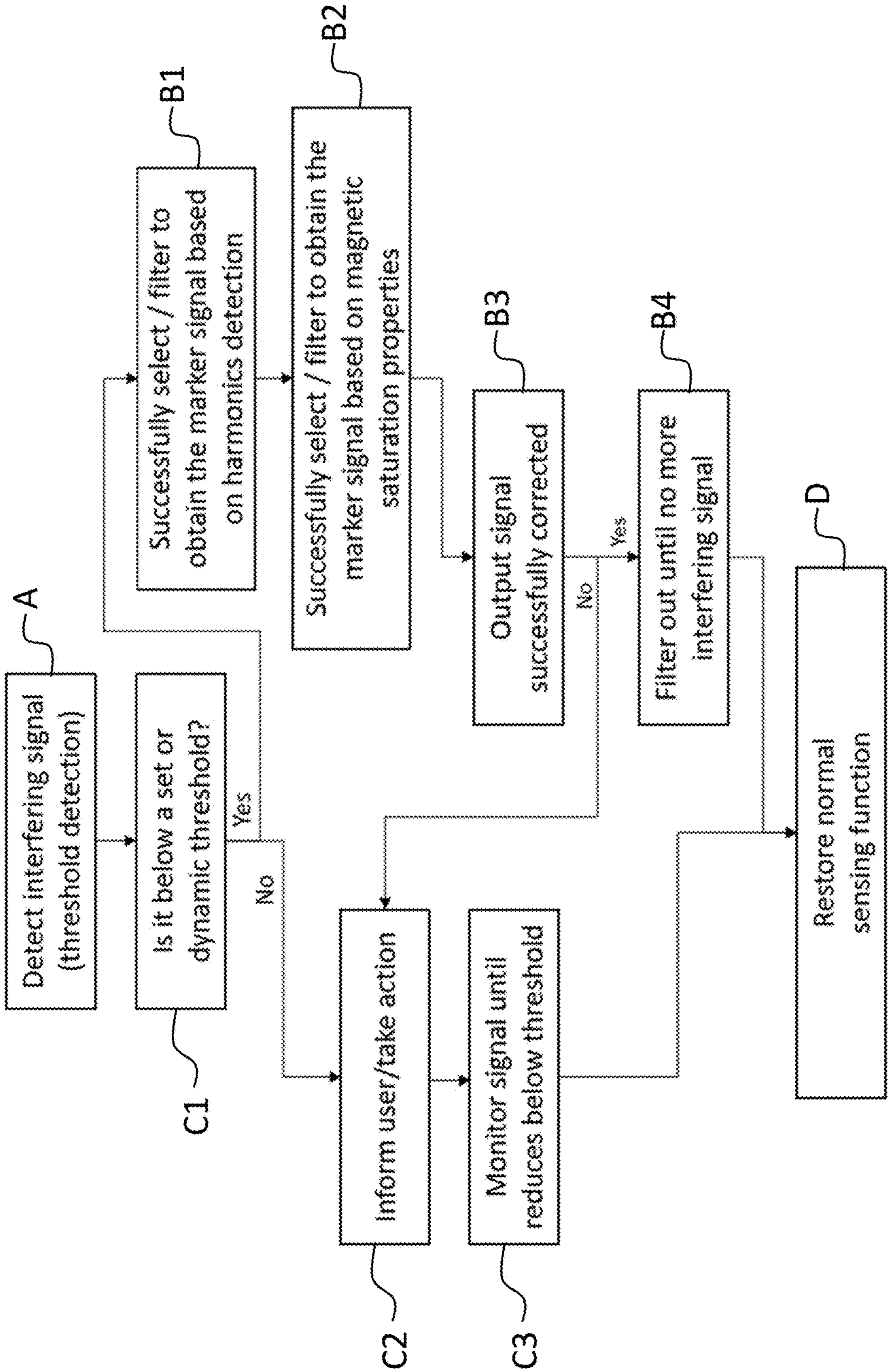
FIG. 9 is a process flow chart showing various steps for managing interference signals using dynamic or variable threshold selection and/or signal selection and/or filtering according to an exemplary embodiment of the disclosure.

As shown in FIG. 9, the method thus typically starts with detecting an interfering signal through a threshold detection step (Step A). With regard to FIG. 9, the various steps shown on the right side, Steps B1, B2, B3, B4, and Step D may be applied to various embodiments and may use various systems and methods including those described in WO 2021/250485 A1, U.S. application Ser. No. 17/926,765, WO 2022/049395 A1, and U.S. application Ser. No. 18/024,448 (the disclosure of each of which is incorporated herein by reference in their entirety) in the event that in Step C1 the level of the interfering signal is below a set or dynamic threshold. In some instances, if there is a borderline threshold, the methods and systems of WO 2021/250485 A1 and U.S. application Ser. No. 17/926,765 (the disclosure of each of which is incorporated herein by reference in their entirety) may applied. If further evaluation and processing is still needed in some embodiments, the methods and systems of WO 2022/049395 A1 and U.S. application Ser. No. 18/024,448 (the disclosure of each of which is incorporated herein by reference in their entirety) may be applied. If the level of the interfering signal is determined to be above the dynamic threshold then the user is alerted (Step C2). The response signal is continued to be monitored (Step C3) until the interfering signal falls below the threshold, when normal sensing function is resumed (Step D).

In various embodiments, the steps disclosed herein, including in FIGS. 9 and 10 may be implemented using a software architecture that may operate on a software module basis. In some embodiments, each software module may be for example, treated as an object in an object-oriented programming environment, and thus each object may have an associated data format. Further, objects having a dedicated purpose will be common across most software and hardware within the same or a related vertical, and hence understanding of common inclusions and data formats within and across these dedicated objects for software and hardware within the same or a related vertical enables the providing of a software architecture that is at least substantially agnostic, i.e., usable across the hardware and software having those same or similar dedicated objects that include the same or similar data. Accordingly, various operations and method disclosed herein may provide a software architecture capable of normalization and use across software and hardware.

In some embodiments, software/software modules discussed herein are exemplary in nature, and the present disclosure may perform its genericized functions across the enumerated and other modules known to those skilled in the art. In some embodiments, a given module may be implemented by any combination of any quantity of software and/or hardware modules or units, and may reside within memory of a computing device such as a client or server device for execution by a processor. Various storage devices may provide one or more tangible computer-readable storage media for storing the basic programming and data constructs that provide the functionality of some embodiments. Software (programs, code modules, instructions) that, when executed by a processor, provide the functionality described herein may be stored in various storage devices such as cloud-based storage. These software modules or instructions may be executed by processing units which may include various computing devices. In various embodiments, a storage system may also provide a repository for storing data used in accordance with the present disclosure.

Also, it is noted that the embodiments may be described as a process which is depicted as a flowchart, a flow diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine-readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, and network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein, the term "memory" refers to any type of long term, short term, volatile, non-volatile, or other storage mediums and is not to be limited to any particular type of memory or number of memories, or type of media upon which memory is stored.

As described in FIG. 10, to assess if the value obtained from the detected signal is in range or exceeds the threshold, it may first be averaged over an amount of time, typically a few milliseconds to several seconds, to obtain a meaningful value and therefore avoid short term variations. For example, in some implementations, a response signal may not be assessed to be saturated unless it remains at a consistent high level for a minimum duration or across multiple successive samples. The average is obtained by calculating a statistical measure or other metric based on the collection of n values during a predefined set of time. In some embodiments, a standard deviation, or other statistical measure may be used.

In some embodiments, the first step of setting or otherwise using a threshold such as a dynamic threshold is to measure signal characteristics, preferably two or more response signal parameters, using a probe or sensor (Step G1). The signal characteristics may be selected from a set of various marker signal parameters. These may include marker signal parameters that are measurable by the probe and that vary over time and the positon of the probe relative to the marker. The parameters may include, without limitation, as follows:

- the magnitude of the signal
- the phase of the signal
- ratios of the magnitudes of the signal for two different characteristics; e.g. the magnitude
- and/or phase of the signal at two or more different frequencies, preferably harmonics
- spatial arrangement of the response around the probe
- relative magnitudes of the signal at different regions around the probe
- orientation of the field at different regions around the probe
- the quality of the modulation of the signal
- ratios of any of the above
- statistical metrics and/or variables or relationships correlated with any of the foregoing or other signal characteristics These values may be used to determine one or more threshold values (Step G2). For example, where two or more parameters of the marker signal have a known relationship to one another, that relationship may be used to define an envelope of valid values, which may be specific to a particular type of marker and/or probe. In turn, the threshold value or a statistical metric that is based on or correlated with it may be measured and/or determined over time (Step G3). Once a suitable value or statistical measure is obtained, the system can compare the value with the threshold (Step G4). Several values can be assessed in parallel. If the value itself or a statistical value correlated therewith is within the range established by the threshold or thresholds, then the system continues through the interference filtering out process (Step G5). If the value or related statistical metric is outside the range defined by the threshold or the thresholds then the user is alerted (Step G6).

In some embodiments, as described above, the system may keep monitoring the marker signal (Step C3) until it is within the range defined by the threshold(s) when the normal sensing functions can be restored (Step D).

In other embodiments, a new dynamic threshold may be set (Step G10) based on another marker signal parameter and the process may be repeated until the interference has been filtered out or has otherwise been managed or the marker has been detected. For example, in some embodiments, the marker signal may include at least two repeating successive portions of different amplitudes, and the method may include processing each successive portion separately. If the value of the signal parameter is valid during at least one of the portions, typically of relatively lower amplitude, normal sensing may continue with the output based only on the portion or portions of the marker signal that are valid, for example using a method disclosed by WO 2022/049395 A1 and U.S. application Ser. No. 18/024,448 (the disclosure of each of which is incorporated herein by reference in their entirety).

If the value or the value of the statistical metric is below a certain threshold during at least one portion of the marker signal, the detection signal can be corrected, for example, using the method described in WO 2021/250485 A1 and U.S. application Ser. No. 17/926,765 (the disclosure of each of which is incorporated herein by reference in their entirety) or used as such if the interference is negligible. In general, the various steps and processes disclosed herein may be performed using the processor, FPGAs, ASICS, electrical circuitry, software, and other components described herein.

In certain instances, the signal is below the threshold, indicating that the interference can be filtered out, but the filtering process fails to filter out the interference. In this case, the system is also able to detect that the output signal has not been successfully corrected, for example if at least one signal characteristic and/or a function of two or more signal characteristics remains outside the range of valid values even after a correction factor has been applied, and therefore the user is informed about the erroneous signal (Step C2) before receiving erroneous feedback. The user may be informed by the changes to the GUI and/or audio output ("AO") described above with regard to FIGS. 5A-D or FIGS. 6A-D, or through other indicia shown on the display screen (26) or through auditory alerts (21).

Figure 8:
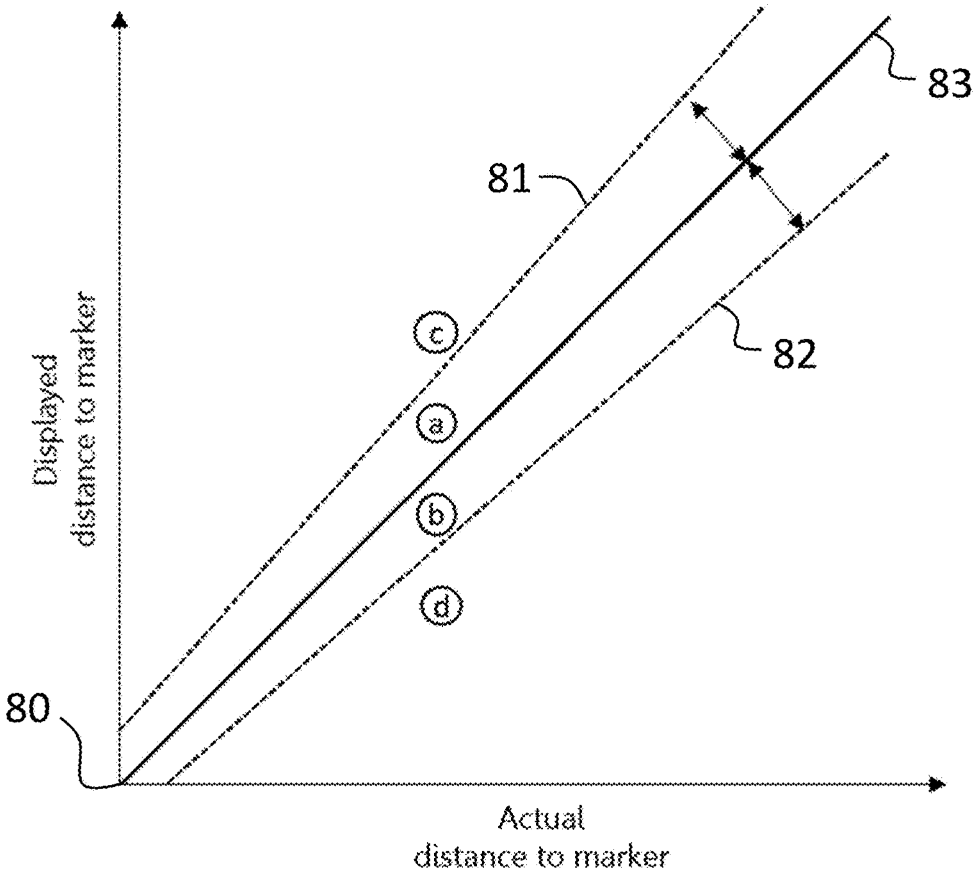
FIG. 8 is a graph showing displayed distance to a marker on a display and the actual distance to the marker and how this relationship varies with sources of interfering/erroneous signal(s) according to an exemplary embodiment of the disclosure.

Determining the threshold over which the system cannot filter out the interference is therefore a determining factor in the activation of the erroneous signal processing in some embodiments. As described in FIG. 8, which shows a plot of displayed distance of the probe (10) to the marker (M) versus actual distance to the marker with thresholds (81, 82) diverging from origin (80) of the plotted position relationship. In some embodiments, the response signal including the detection signal and the interfering signal can be substantially offset from the value intended to be correct (83)

according to representation of various thresholds, regions of overlap, and other information illustrated in the graph of FIG. 8. With regard to FIG. 8, various areas a, b, c, and d are labelled or identified relative to the graph as shown by the corresponding encircled letters a, b, c, and d for each respective area.

Four or more areas may be distinguished using the referenced representation distance to the marker and actual distance to the marker in FIG. 8, which may be obscured based on interference or other erroneous signals. Two areas a and b are close to the value intended to be correct (83) and represent normal readings within a margin of error, which can usually be corrected with various methods such as for example those described in WO 2021/250485 A1 and U.S. application Ser. No. 17/926,765 (the disclosure of each of which is incorporated herein by reference in their entirety). Two areas c and d are further away from the value intended to be correct (83) and are respectively increased or decreased beyond the threshold level (81, 82); determining that the interference is too strong to be processed. Areas a and b of the graph of FIG. 8 match with Zone 4 of FIG. 7. This is where the interference is negligible or can be filtered out. The various details of FIG. 8 and the zones described herein may be encoded in one or more software modules or hardware that is configured to perform the relevant steps as part of the operation of the detection system/base station.

Areas c and d of the graph of FIG. 8 match with Zones 1, 2, 3, 5 and 6 of FIG. 7. In these cases, the interfering signal can be filtered out if the detection signal is sufficiently strong compared to the interfering signal as per Zones 1, 2 and 6. If the interfering signal is too strong to be filtered out but there is still a detectable detection signal, the system can identify that the output signal is erroneous and therefore inform the user. The system may not be able to identify the erroneous signal output if the probe is away from the site of interest where the marker or tracer is located but close from the source of interfering signal as per Zone 5 but this may not cause confusion as the probe will not be in use in this configuration.

The areas described in FIG. 8 diverge away from the origin (80) of the graph, this is due to the detection signal being smaller at further distances from the detection probe, meaning that the signal to noise ratio is reduced and the signal is therefore likely to be less accurate and more susceptible to interference. The thresholds (81, 82) separating area a from area c and area b from area d can use several types of data, depending on the detection method used.

The detection signal includes one or more characteristics such as magnitude, phase, frequency, or modulation. The erroneous signal assessment system can monitor any of these characteristics to assess if they are within the right range. It is also possible to assess if several of these characteristics are within the right range and further assess the resulting level of confidence from combining the assessment of each of these characteristics. Preferably, a ratio between, or mathematical function of, two or more characteristics can also be used in accordance with certain aspects of the present disclosure to assess if the response signal is within the proper range, for example the ratio of the magnitudes or phases of two different frequencies in the signal. Suitably, the different frequencies may be harmonics, for example of a driving field. In some implementations, the harmonics may include the first and third harmonics, particularly where the marker is magnetic and the probe is a susceptometry probe, as disclosed in more detail below.

AC Susceptometry Detection

An AC susceptometry detection-based method or system detects magnetically responsive materials and metals by generating an alternating magnetic field and measuring the response from a magnetically responsive marker (M). The response may be linear, that is at the same frequency as the drive field, or harmonic, that is also containing components at frequencies which are harmonics of the drive frequency, especially where the marker is made of magnetic material with a Large Barkhausen Jump, in which case the driving field may have an amplitude above or below the threshold at which the domains of the LBJ material flip their polarity. Sources of interference (I) include materials which also generate a magnetic response or distortion of the magnetic field. These could include surgical tools or instruments, metallic implants such as other markers joints made from magnetic, particularly ferrous or metallic materials. When they are near the AC susceptometry probe (10), they can create interfering signals, which can mimic the response from a marker or even drown the signal. If there is a large amount of material close to the probe, the level of interfering signal can be sufficiently large to saturate the input stage of the detection probe.

The interfering signals from metallic or magnetic materials may be detected and/or identified according to the present disclosure by assessing one or more of the following characteristics of the AC susceptometry response signal or combinations thereof; preferably two or more parameters of the response signal:

magnitude of the response at the fundamental (drive) frequency the phase of the response at the fundamental (drive) frequency the magnitude of the response at one or more harmonic frequencies the phase of the response at one or more harmonic frequencies ratios of the magnitudes and/or phases of the response at two or more different frequencies, e.g. harmonics spatial arrangement of the response around the probe Where the marker (M) is formed of an LBJ material, the interfering signals from metallic or magnetic materials may be detected and/or identified by assessing the value of a ratio of the amplitudes of two or more harmonics, especially the first and third harmonics of the response signal from the marker. The marker is known to respond to a driving field in a particular way with a certain relationship between the amplitudes of the different harmonics. If the ratio is assessed to have a value which does not accord with the known relationship between the harmonic amplitudes for a given marker, then the response signal may be determined to include an interfering signal. Correction may be attempted as disclosed herein and if the value of the ratio remains outside the range of valid values for the marker according to the predetermined relationship between the harmonics, the response signal may be assessed to be erroneous and a suitable alert output as disclosed herein.

Permanent Magnet Field Detection

Permanent magnet field detection-based systems and methods may include one or more magnetic field sensors configured to detect the field from an implant that includes a permanent magnet marker (M). An array of magnetic field sensors can also be provided to assess the spatial arrangement of the field in the region of the probe. The detection probe (10) is vulnerable to interference from any source of magnetic field (I) and from ferrous or metallic materials that might distort a magnetic field locally. Sources of magnetic field may include magnets found in the operating theatre, such as magnetic instrument mats and drapes for holding surgical tools, and magnetic implants such as those used in the ports of breast expanders, or in cochlear implants or dental implants. Fields from an MRI scanner are also potential sources of interfering magnetic fields. Surgical instruments and other metallic objects near the probe may also distort the field coming from a permanent magnet marker.

The interfering signals from sources of magnetic field or objects distorting the field may be identified by assessing any of the following characteristics of the magnetic field detection signal or combinations thereof; preferably two or more parameters of the response signal:

- magnitude of the field signal
- relative magnitudes of the field signal at different regions around the probe
- orientation of the field at different regions around the probe
- combinations of the above to allow spatial arrangement of the field in the region of the probe to be assessed For example, if a large field from a magnetic instrument drape is causing distortion of the signal, the presence of the interference may be identified by assessing the spatial field distribution around the probe with an array of field sensors. The large interfering field may be detectable in a larger region than the short range local field from a permanent magnet marker, thus allowing the interference to be identified.

Electromagnetic Radiation

In some embodiments, a detection system may use radar detection of an implanted reflector. Improved directionality is obtained by including a switch in the reflector which changes one or more parameters or effective parameters such as size of the reflector in response to illumination. Thus, an IR source on the detection probe (10) can be used to modulate the radar response for improved directionality of sensing. The system benefits good contact between the probe and tissue for the IR radiation to couple into the tissue effectively. Marker detection with this system is vulnerable to interference from other sources of IR radiation (I) such as incandescent light sources, to radar reflective surfaces in the vicinity of the marker and detection probe, such as surgical instruments or implanted devices, and to any other sources of electromagnetic transmissions at the same frequency as the radar. Loss of good contact between the probe and tissue may also result in a distortion to the signal.

The interfering signals from sources of incandescent light or radar interference can be identified by assessing any of the following characteristics of the detection signal or combinations thereof; preferably two or more parameters of the response signal:

- the magnitude of the radar signal
- the phase of the radar signal
- the quality of the modulation of the radar signal by assessing the relative magnitudes of the 'on' and 'off' parts of the cycle For example, if the presence of an incandescent light is interfering with the signal by switching on the photodiode in the marker, the relative magnitude of the radar response between the 'on' and 'off' parts of the cycle will be altered because the interfering light switches the photodiode partially on all the time. This variation in the quality of the modulation can be detected and the user can be alerted.

RFID Detection

Some systems use the electromagnetic field for the detection of an implanted marker (M). In one example of this RFID system, the analogue drive circuit excites a coil to generate an RF signal which can excite a resonance in a passive integrated transponder (PIT) tag, also commonly known as an RFID tag. The signal from the PIT tag is demodulated and filtered before being transmitted to the base unit (20). Marker detection with this system is vulnerable to interference from other electromagnetic sources (I) such as electromagnetic absorbing objects, electromagnetic interference or Near Field Communication devices in the vicinity of the marker and detection probe. RFID markers of this sort typically have directions in which there is little or no response because the marker orientation with respect to the interrogating electromagnetic signal is not favourable i.e., there are dead spots in the response. For example, transverse the axis of a coil in the marker, the coil will not be able to couple enough energy from the incident waves to power the RFID circuit properly and the response will be poor.

The interfering signals from electromagnetic absorbing objects, electromagnetic interference or Near Field Communication devices can be identified by assessing any of the following characteristics of the magnetic field detection signal or combinations thereof; preferably two or more parameters of the response signal:

- the quality of the data coming from the marker e.g., the identification number of the marker
- the magnitude of the reflected RF wave or backscatter
- the phase of the reflected RF wave or backscatter For example, if the handheld probe (10) is approaching the RFID marker from a direction where there is a dead spot, one or more additional detection antennas in the handheld probe which are at a different angle to the marker may be used to detect the marker and identify it or to alert the user that the orientation is not favourable.

EM Tag Detection

In some embodiments, an EM tag-based detection system or method may use a magnetic or electromagnetic field to excite an implanted marker (M). The field may be generated by a coil, for example, in a mat underneath the patient (not shown). The marker emits sidebands at specific frequencies when it is excited by the field. The system detects the sidebands via one or more detectors which may also be positioned within a mat underneath the patient. The system further includes a tag similar to the marker which is attached to a surgical tool. By interrogating the signals from the detectors, the position and relative positions of the marker and the tag on surgical tool may be calculated and communicated to the user.

An EM tag-based system may be susceptible to interference from ferrous, magnetic or metallic objects (I), which may distort or reflect magnetic fields or electromagnetic waves. For example, a ferrous or metallic object surgical tool, which is between the marker or tag and the exciting coil, may distort the signal emitted from the marker or from the tag, and a metallic or ferrous object between the marker or tag and one or more of the detectors may distort the received signal at the field detector.

The interfering signals from ferrous or magnetic or metallic objects distorting the detected field can be identified by assessing any of the following characteristics of the detector signal or combinations thereof; preferably two or more parameters of the response signal:

- magnitude of the field signal at a detector
- phase of the field signal at a detector
- modulation of the field signal
- magnitude or phase of one or more sidebands at the detector
- relative values of any of the above characteristics signal from one or more different field detectors For example, if a ferrous surgical tool comes between the marker and a field detector, the magnitude of the signal at that detector may be reduced. If there are sufficient field detectors positioned at separate locations around the marker, the signal from the marker may still be detected at other detectors. By interpreting these signals to identify the position of the marker, the system can detect that the expected signal from the affected detector is not present. With sufficient redundancy, the erroneous signal can be discarded. If the interference is such that the position of the marker cannot be determined accurately, then the user can be alerted to the presence of an interfering signal.

Passive Markers and Tracers

In some embodiments, no drive signal is used in the probe (10) because the sensor in the probe used to detect a given marker is a passive sensor. This may apply to various tracers and markers, such as for a radioactive marker or tracer that may be detected passively without the need for a probe signal to extend to and interrogate the marker. Instead, in various embodiments, the probe passively detects the signals coming from a given passive marker or sensor.

In the handheld detection probe (10) for the exemplary passive tracer or marker (M) there is a radioactive signal detector and a signal processing unit. This may also apply to other passive tracers or markers, but with different sensors disposed in the probe unit. In the base unit (20), the signal may be processed by the analogue signal processing unit (43), which is specific to the marker detection technology, before being digitised by the analogue to digital converter (ADC) (54). Further signal processing may also happen in the digital signal processing unit (42), and this may involve any of filtering, demodulation, a lock-in amplifier and other means of isolating the signal from sources of noise and converting it into an output signal. The microcontroller (48) communicates the output signal (45) to the display (26) and audio output (loudspeaker) (21) to give the user an indication of the proximity of the probe (10) to the tracer or marker (M), position of the tracer or marker, or distance from the tracer or marker to the probe.

The radioactive tracer or marker detection probe (10) may include a radiation detector (19) to generate a small electrical signal in response to incident radiation, a pre-amplifier (18) to increase the magnitude of the signal, and a signal processing unit to filter or otherwise isolate the signal from unwanted noise. The signal is then transmitted to the base unit (20), either via a cable ('wired' probe) or via a wireless link. The tracer signal then connects to the main processing unit (42) via the ADC (54) and the signal is processed as described herein including in the descriptions of FIGS. 9 and 10.

A given detection system may be susceptible to interference associated with a shine-though effect or similar effects and outcomes on the system. For example, in sentinel lymph node (SLN) biopsy, a radioisotope tracer is typically injected at the site of the primary tumour before it is drained through the direct lymphatic drainage pathway to the first lymph node or nodes which are most likely to harbour metastasis. Then, the radioactive nodes identified using the handheld detection probe are dissected. Although sometimes the primary tumour radioactivity obscures nearby radioactive SLNs, therefore limiting accurate SLN detection. Alternatively, the radioactive primary tumour could show a signal of an intensity similar to the one typically detected from the SNLs where the radioisotopes migrated although more diffuse.

Without proper interpretation, the shine-through effect could lead the practitioner to dissect healthy nodes. Typically, the primary tumour site will contain a high number of radioisotopes, even after sufficient migration to the lymph nodes is complete, potentially giving an apparent high signal for the lymph nodes to be assessed due to the shine-through effect. The proposed system aims at avoiding false signals cause by shine-through effects by alerting the user. This interfering signal can be identified when the signal detected by the probe is superior to a predetermined threshold corresponding to the maximum signal that a lymph node impregnated by radioisotope is expected to release. This interfering signal can also be detected by assessing the spatial diffusion of the signal, i.e., if the signal is not focused then it can be identified as being of interfering nature.

In other settings, a radioactive seed can be placed in the tumour in addition to the injection of a radioactive tracer. This would further increase the undesirable shine-through effect.

Control Switches and Electronic Components and User Feedback

The various thresholds of the characteristics of the signal allowing the assessment of its quality can be modified or removed by using on/off or modulating functions. Examples of user controls include switches, rotary encoders, potentiometers, voice control functions, or touchless functions like motion gesture detection. They can be positioned on the probe, box, and/or pedal. These controls can be used individually or in combination.

The user can also be alerted of an erroneous signal through various feedbacks. Examples of some visual feedback generated by changing one or more (or all) of a set of graphical elements displayed as well as changes to audio output provided as part of the localization process are depicted in FIGS. 5A-D and 6A-D. In various embodiments, these images shown in FIGS. 5A-D and 6A-D show a probe (10) approaching a marker (M) with various curves or straight lines corresponding to different distances or other geometric positions relative to the marker. The marker and other positions that the probe (10) moves relative to may be shown with curved lines such as arc segments, circle segments, elliptical segments and other visual representations without limitation. In various embodiments, the visual depiction of the probe (10) may change and the graphic file(s) associated with a given probe (10) may be stored in the writable memory (14) that is part of the probe (10) and configured for electronic reading and processing by a detection system such as a base unit (20).

Various visual representations such as images, lines, pixels, real-world images of patient tissue, icons, cartoons, renderings, 2-D graphical representations, 3-D graphical representations and other displayable information may be shown on a given display (26) to support detecting and/or localizing a marker. Any of the foregoing (and all other figures and related descriptions used to detect and localize a marker or tracer) and other information may be changed, modified, replaced, added-to, animated or otherwise transformed to indicate the occurrence of interference or another erroneous signal or other information of interest to a user.

In some embodiments, as part of displaying interference or an erroneous signal, the probe position on the display (26) may be frozen, flash, or otherwise change in appearance. In some embodiments, the visual display and distance information may be animated and include color changes to show proximity to the marker such as with colors associated with proximity and others showing that the probe is farther away from the marker or tracer. In some embodiments, color changes or other changes to one or more of graphical elements may be used to indicate an event of interest such as the occurrence of interference, an error signal, an erroneous signal or other information or events of interest to the user. In some embodiments, all or some of the colors of the visual elements shown on the display (26) may all turn grey or be changed such that a solid part of a visual element is replaced with hatching, dotted lines, or another pattern. In one embodiment, the change to the display 63 of FIG. 6C that is indicative of an interference signal or another event of interest may also be modified such that some or all of the colors displayed change to grey or another color or pattern or a system standby state. In some embodiments, the detection system may display the probe (10) relative to other on screen display elements (or a lack thereof) when no marker detection is occurring such as when the probe is far away from the marker. The information displayed by the system when the probe is at a set distance from the marker such that the system is effectively in standby mode until the probe moves closer to the marker may also be reverted to when interference or another event of interest is detected in some embodiments. In some embodiments, when the probe is a distance from the marker such as a distance greater than about 40 to about 100 mm, or in some embodiments greater than about 40 mm, a standby display (63) may be shown on the screen (26) which may use various color palettes and color selections including gray, black and white, grayscale, and any other possible color palettes. Reversion to the standby display simplifies the process of alerting an end user to interference or another event.

The system may turn off all signal output until the signal feedback is restored to normal function or provide a warning using sound alerts, a display message, haptic feedback or by continuing to display the output signal but with a distinct colour (for example in red or another colour suitable for indicating that the user needs to reposition the probe or otherwise convey to the user that the probe is triggering on an erroneous signal or other problem in the location of use). These feedback mechanisms can be used individually or in combination.

Further, the various systems, probes, control systems, actuators, transducers, user feedback sources, controllers, component, software and parts of the foregoing can be used with any suitable diagnostic or surgical guidance system and other methods and conjunction with other devices and systems without limitation.

While various details have been set forth in the foregoing description, it will be appreciated that the various aspects of the techniques for operating a diagnostic and/or surgical guidance system suitable for identifying, localizing, tracking, and detecting position of one or more implanted markers may be practiced without these specific details. One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

The disclosure of PCT application having international publication no. WO 2021/250485 A1 entitled "Systems and Methods for Detecting Magnetic Markers for Surgical Guidance" and the related co-pending U.S. Patent Application having application Ser. No. 17/926,765 and entitled "Systems and Methods for Detecting Magnetic Markers for Surgical Guidance" are each incorporated by reference in their entirety. The disclosure of PCT application having international publication no. WO 2022/049395 A1 "Systems and Methods for Detecting Magnetic Markers for Surgical Guidance" and the related co-pending U.S. Patent Application having application Ser. No. 18/024,448 and entitled "Systems and Methods for Detecting Magnetic Markers for Surgical Guidance" are each incorporated by reference in their entirety.

Further, while several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, and equivalents.

For conciseness and clarity of disclosure, selected aspects of the foregoing disclosure have been shown in block diagram form rather than in detail. Some portions of the detailed descriptions provided herein may be presented in terms of instructions that operate on data that is stored in one or more computer memories or one or more data storage devices of the base station or the one or more processors or microprocessors operative therein (e.g. floppy disk, hard disk drive, caches, random access memory, and other optical and magnetic storage devices and media). Such descriptions and representations are used by those skilled in the art to describe and convey the substance of their work to others skilled in the art.

In general, an algorithm refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states. The various methods steps disclosed herein may be implemented or programmed as algorithms, data structures, and instructions that may operate upon inputs from data channels and generate outputs that contain various types of data such as user actionable data, user feedback signals, information, and images.

Unless specifically stated otherwise as apparent from the foregoing disclosure, it is appreciated that, throughout the foregoing disclosure, discussions using terms such as "processing" or "computing" or "calculating" or "thresholding" or "determining" or "displaying" or the like, refer to the action and processes of a computer system, processor-based base station, or similar electronic computing device that manipulates and transforms data represented as physical (electronic) quantities within the computer system's registers and memories into other data similarly represented as physical quantities within the computer system memories or registers or other such information storage, transmission or display devices.

In some implementations described herein, logic and similar implementations may include software or other control structures. Electronic circuitry, for example, may have one or more paths of electrical current constructed and arranged to implement various functions as described herein. In some implementations, one or more media may be configured to bear a device, threshold, signal, or other detectable implementation when such media holds, or transmits, device, threshold, signal, or other detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. In various embodiments, one or more software applications or modules may be used to display or stop displaying portions of a user interface screen, an animation, and/or auditory signals to help guide an end user performing one or more procedures relating to tissue in the vicinity or a marker or tracer. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission, wired transmission, wireless transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein including those relating to threshold selection; dynamic thresholds; marker or tracer signal selection. In some variants, operational or other logical descriptions herein may be expressed as source code, and compiled or otherwise invoked as an executable instruction sequence. In some contexts, for example, implementations may be provided, in whole or in part, by source code, such as C++, scripting languages, or other code sequences.

In other implementations, source or other code implementation, using commercially available and/or techniques in the art, may be compiled//implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an ASIC, an FPGA, or other electronic-component based circuit). Those skilled in the art will recognize how to obtain, configure, and optimize suitable transmission or computational elements, material supplies, actuators, or other structures in light of these teachings.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein, "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. In one form, several portions of the subject matter described herein may be implemented via application specific integrated circuits (ASIC), a field programmable gate array (FPGA), a digital signal processor (DSP), or other integrated formats. However, those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

The terms "approximately" and "about" may be used to mean within +20% of a target value in some embodiments, within +10% of a target value in some embodiments, within +5% of a target value in some embodiments, and yet within +2% of a target value in some embodiments. The terms "approximately" and "about" may include the target value.

In the claims, as well as in the specification above, all transitional phrases such as "comprising," "including," "carrying," "having," "containing," "involving," "holding," "composed of," and the like are to be understood to be open-ended, i.e., to mean including but not limited to. The transitional phrases "consisting of" and "consisting essentially of" shall be closed or semi-closed transitional phrases, respectively.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

The use of headings and sections in the application is not meant to limit the disclosure; each section can apply to any aspect, embodiment, or feature of the disclosure. Only those claims which use the words "means for" are intended to be interpreted under 35 USC 112, sixth paragraph. Absent a recital of "means for" in the claims, such claims should not be construed under 35 USC 112. Limitations from the specification are not intended to be read into any claims, unless such limitations are expressly included in the claims.

Embodiments disclosed herein may be embodied as a system, method or computer program product. Accordingly, embodiments may take the form of an entirely hardware embodiment, an entirely software embodiment (including firmware, resident software, microcode, etc.) or an embodiment combining software and hardware aspects that may all generally be referred to herein as a "circuit," "module," or "system." Furthermore, embodiments may take the form of a computer program product embodied in one or more computer readable medium(s) having computer readable program code embodied thereon.

Although aspects of the disclosure herein have been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the scope of the disclosure as defined by the appended claims.

The invention claimed is:

1. A method of localizing a marker in the presence of one or more interfering signals using a hand-held probe in communication with a non-imaging marker localization system, the method comprising:

detecting a marker signal using the hand-held probe;

measuring, using the hand-held probe, a set of parameters of the marker signal, the parameters varying over time and with the position of the hand-held probe relative to the marker;

determining a dynamic range of values of a variable of the marker signal, wherein the variable is selected from the set of parameters of the marker signal, wherein the dynamic range of values vary according to measured values of the set of parameters of the marker signal;

detecting an interfering signal using the hand-held probe by measuring the value of the variable of the marker signal, and comparing the measured value of the variable of the marker signal with the dynamic range of values of the variable;

determining the marker signal to be an erroneous signal when the measured value of the variable falls outside the dynamic range of values; and generating user feedback indicating the erroneous signal.

2. The method of claim 1, wherein the user feedback comprises removing one or more on screen graphical user interface depictions of a portion of the hand-held probe or target marker area when the measured value of the variable of the marker signal falls outside the range of values of the variable.

3. The method of claim 1, wherein the user feedback comprises a change or cessation of auditory feedback presented to user when the measured value of the variable of the marker signal falls outside the range of values of the variable.

4. The method of claim 1, further comprising repeating the comparing step until the measured value of the variable of the marker signal falls within the range of values of the variable.

5. The method of claim 4, further comprising resuming marker detection without monitoring for an interference signal.

6. The method of claim 4, wherein the detecting of an interfering signal is performed relative to a zone or region within which the interfering signal and the marker signal overlap.

7. The method of claim 6, wherein the hand-held probe is a magnetic susceptometry detection probe.

8. The method of claim 1, further comprising selecting a new variable from the set of parameters of the marker signal when the measured value of the variable falls outside the range of values of the variable.

9. The method of claim 1, wherein the set of parameters of the marker signal comprises two or more parameters selected from a magnitude of the marker signal, a phase of the marker signal, ratios of the magnitude and/or phase of the marker signal at two or more different frequencies, a spatial arrangement of the signal around the hand-held probe, relative magnitudes of the signal at different regions around the probe, an orientation of the signal at different regions around the probe, a quality of modulation of the signal, ratios of any of the foregoing, and statistical metrics and/or variables or relationships correlated with any of the foregoing.

10. The method of claim 1, wherein the—variable is a signal-to-noise ratio (SNR) and the dynamic range of values varies with SNR, wherein the SNR is determined using a strength of marker signal relative to interference.

11. The method of claim 1 further comprising in response to a selected variable not being within a desired range, selecting a new dynamic variable that is not subject to signal interference as probe changes position.

12. The method of claim 1 further comprising distinguishing between a first zone and a second zone to inform user actions relative to a user interface, wherein a first level of overlap between a detection signal and interference signal in the first zone differs from a second level of overlap between a detection signal and interference signal in the second zone.

13. The method of claim 1 further comprising displaying a standby mode display when an interference signal is detected, the standby mode display comprising a probe representation and a marker representation, wherein the erroneous signal is an interference signal.

14. A method of localizing a marker in the presence of one or more interfering signals using a hand-held probe in communication with a non-imaging marker localization system, the method comprising:

detecting a marker signal using the hand-held probe;

measuring, using the hand-held probe, a set of parameters of the marker signal, wherein the set of parameters of the marker signal vary over time and with the position of the hand-held probe relative to the marker;

selecting a variable of the marker signal, wherein the variable is selected from the set of parameters of the marker signal;

determining a dynamic range of values of the variable of the marker signal, wherein the dynamic range of values vary according to measured values of the set of parameters of the marker signal, wherein each parameter of the marker signal of the set of parameters are measurable by the hand-held probe and vary over time and with a position of the hand-held probe relative to the marker;

detecting an interfering signal using the hand-held probe by measuring the value of the variable of the marker signal;

comparing the measured value of the variable of the marker signal with the dynamic range of values of the variable; and determining the selected variable is not within a desired range and, in response thereto, selecting a new dynamic variable that is not subject to signal interference when localizing the marker.

15. The method of claim 14 wherein determining that the selected variable is not within a desired range is performed by comparing the measured value of the variable of the marker signal with the dynamic range of values of the variable.

16. The method of claim 14 further comprising distinguishing between a first zone and a second zone to inform user actions relative to a user interface, wherein a first level of overlap between a detection signal and interference signal in the first zone differs from a second level of overlap between a detection signal and interference signal in the second zone.

17. The method of claim 14 further comprising displaying a standby mode display when an interference signal is detected, the standby mode display comprising a probe representation and a marker representation.

* * * * *